United States Patent
Kiesel et al.

(10) Patent No.: US 11,584,662 B2
(45) Date of Patent: Feb. 21, 2023

(54) SYSTEMS AND METHOD FOR CORRECTION OF POSITIONALLY DEPENDENT ELECTROMAGNETIC RADIATION DETECTED FROM OBJECTS WITHIN A FLUID COLUMN

(71) Applicant: Inguran, LLC, Navasota, TX (US)

(72) Inventors: Peter Kiesel, Palo Alto, CA (US); Todd Karin, Berkeley, CA (US); Kenneth Michael Evans, College Station, TX (US)

(73) Assignee: Inguran, LLC, Navasota, TX (US)

( * ) Notice: Subject to any disclaimer, the term of this patent is extended or adjusted under 35 U.S.C. 154(b) by 357 days.

(21) Appl. No.: 16/820,585

(22) Filed: Mar. 16, 2020

(65) Prior Publication Data
US 2021/0285882 A1 Sep. 16, 2021

(51) Int. Cl.
| | | |
|---|---|---|
| C02F 1/32 | (2006.01) | |
| G01N 21/64 | (2006.01) | |
| G01N 15/14 | (2006.01) | |
| G01N 33/50 | (2006.01) | |
| G01N 15/10 | (2006.01) | |

(52) U.S. Cl.
CPC ............. *C02F 1/325* (2013.01); *G01N 15/14* (2013.01); *G01N 15/1404* (2013.01); *G01N 15/1429* (2013.01); *G01N 15/1434* (2013.01); *G01N 15/1436* (2013.01); *G01N 15/1459* (2013.01); *G01N 21/645* (2013.01); *G01N 21/6486* (2013.01); *G01N 33/5005* (2013.01); *G01N 2015/1006* (2013.01); *G01N 2021/6463* (2013.01)

(58) Field of Classification Search
CPC .... C02F 1/325; G01N 15/14; G01N 15/1404; G01N 15/1429; G01N 15/1434; G01N 15/1436; G01N 15/1459; G01N 21/645; G01N 21/6486; G01N 33/5005; G01N 2015/1006; G01N 2021/6463
USPC .................................................. 356/310, 300
See application file for complete search history.

(56) References Cited

U.S. PATENT DOCUMENTS

| | | | |
|---|---|---|---|
| 4,327,972 | A | 5/1982 | Brunsting |
| 6,532,061 | B2 | 3/2003 | Ortyn et al. |
| 8,767,212 | B2 | 7/2014 | Kanda et al. |
| 8,885,153 | B2 | 11/2014 | Pittaro et al. |
| 2011/0222062 | A1 | 9/2011 | Martini et al. |
| 2012/0085933 | A1 | 4/2012 | Doi et al. |
| 2014/0273192 | A1 | 9/2014 | Sharpe et al. |
| 2015/0233704 | A1 | 8/2015 | Martini et al. |
| 2019/0040356 | A1 | 2/2019 | Durack et al. |

OTHER PUBLICATIONS

PCT International Search Report and Written Opinion dated Jul. 8, 2021 in related PCT Application No. PCT/US21/22381.

*Primary Examiner* — Md M Rahman
(74) *Attorney, Agent, or Firm* — Ryan Christensen; Hashim Rahman

(57) ABSTRACT

A discrimination system that forms a fluid column and interrogates objects within the fluid column with an excitation source. An optical arrangement collects output electromagnetic radiation emanating from the excited objects disposed within the fluid column and directs the output electromagnetic radiation to a detector. An analyzer reduces the positional dependency of the detected intensity by normalizing the value based on the position of each object.

32 Claims, 16 Drawing Sheets

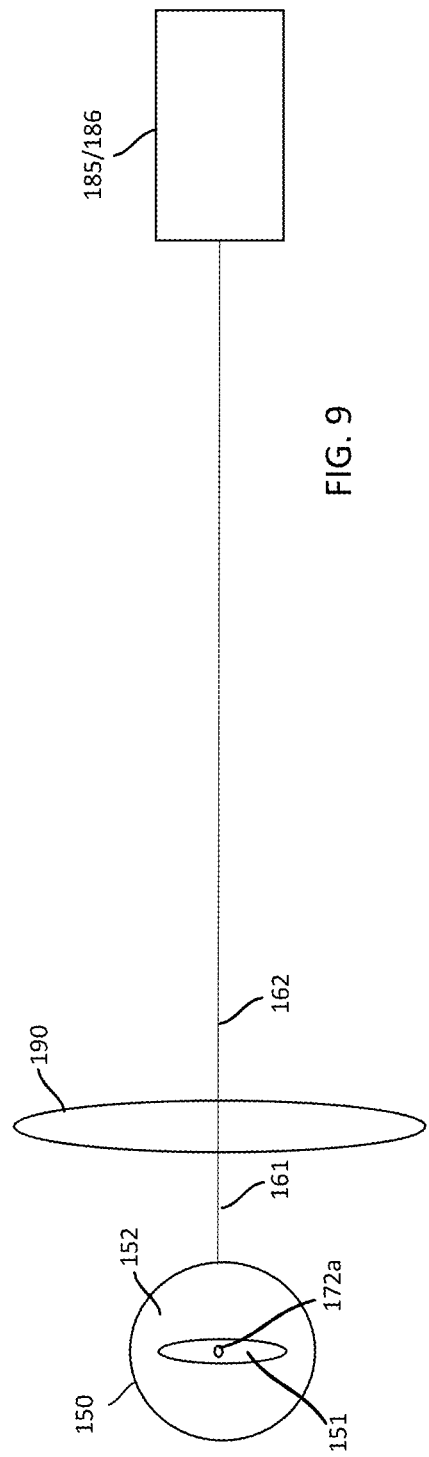
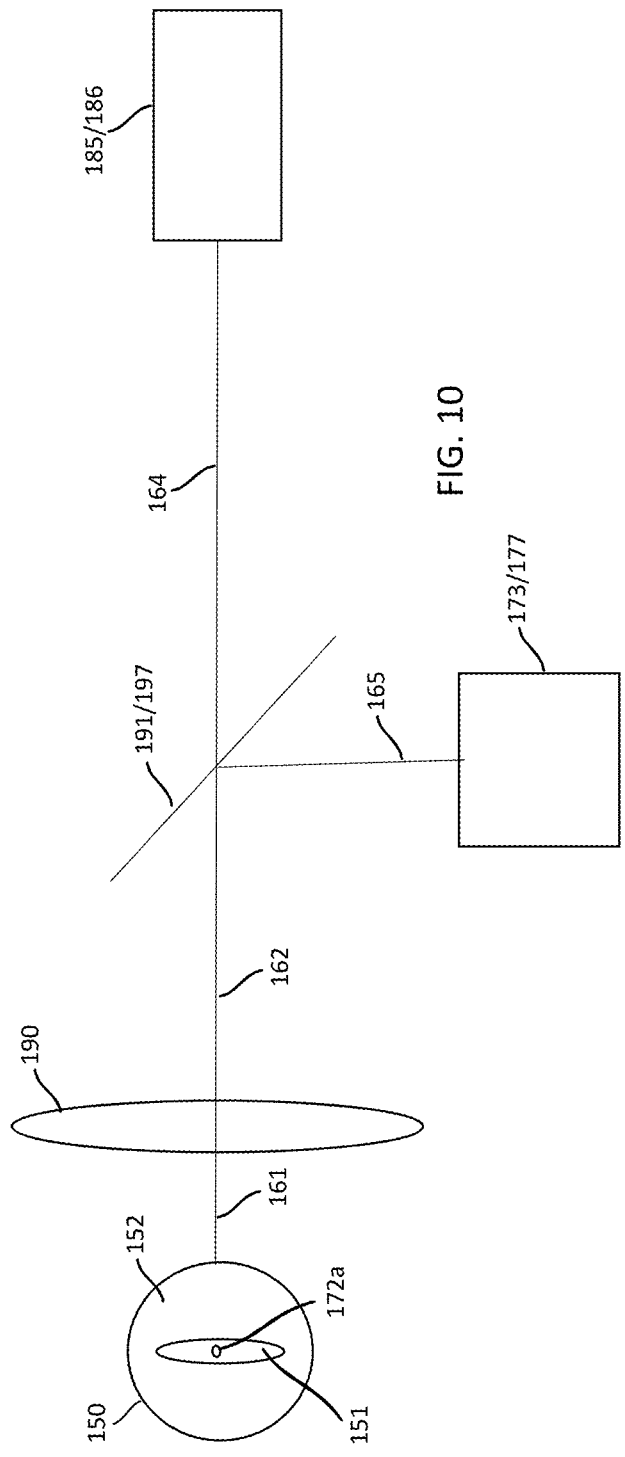

SYSTEMS AND METHOD FOR CORRECTION OF POSITIONALLY DEPENDENT ELECTROMAGNETIC RADIATION DETECTED FROM OBJECTS WITHIN A FLUID COLUMN

BACKGROUND

Object discrimination devices and techniques distinguish between objects of different types, such as objects with different characteristics. These devices and techniques are particularly useful to analyze and even sort cells according to specified characteristics of interest. Some cell sorting approaches rely on light emanating from the cells, or stained cells, to determine their type. In some implementations, cells traveling in a column of fluid are exposed to an excitation source to generate an output electromagnetic radiation for detection. Cells of a first type, or having a particular characteristic, produce output electromagnetic radiation that is different in some characteristic, e.g., wavelength and/or intensity, as compared to other cells. Such differences serve as the basis for cell type discrimination and sorting.

SUMMARY

Some embodiments are directed to a discrimination system for discriminating between different types of objects based on electromagnetic radiation emanating from objects disposed within a fluid column. A fluid column forming structure creates a fluid column containing objects at differing positions within the fluid column and an excitation source generates excitation electromagnetic radiation directed toward objects in the fluid column at a measurement region. Objects within the fluid column emanate output electromagnetic radiation in response to the excitation electromagnetic radiation. An optical arrangement collects output electromagnetic radiation from the objects and a detector generates an electrical signal responsive to the intensity of the output electromagnetic radiation. An analyzer includes instructions stored thereon i) to normalize the intensity of the output electromagnetic radiation represented in the electrical signal based on the position of the object in the fluid column, and ii) to discriminate a first type of object from other objects.

In accordance with some embodiments of a detection system, an optical arrangement collects output electromagnetic radiation from objects in a fluid column and a detector generates an electrical signal responsive to the intensity of the output electromagnetic radiation collected by the optical arrangement. An analyzer has instructions stored thereon i) to normalize the intensity of the output electromagnetic radiation represented in the electrical signal based on the position of the object in the fluid column, and ii) to discriminate a first type of object from other objects.

In accordance with other embodiments, a method of discriminating objects begins by creating a fluid column containing objects at differing positions within the fluid column. Excitation electromagnetic radiation is directed toward objects in the fluid column at a measurement region. Objects at the measurement region emanate output electromagnetic radiation in response to the excitation electromagnetic radiation, which is collected and used to generate an electrical signal responsive to the intensity of the output electromagnetic radiation. The intensity of the output electromagnetic radiation represented in the electrical signal are normalized based on the position of the object in the fluid column and a first type of object is discriminated from other objects.

BRIEF DESCRIPTION OF THE DRAWINGS

FIG. 9 provides a schematic for an embodiment including position and intensity detection from a single detector.

FIG. 10 provides a schematic for an embodiment including a first detector for detecting intensity and a second detector for determining object position.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
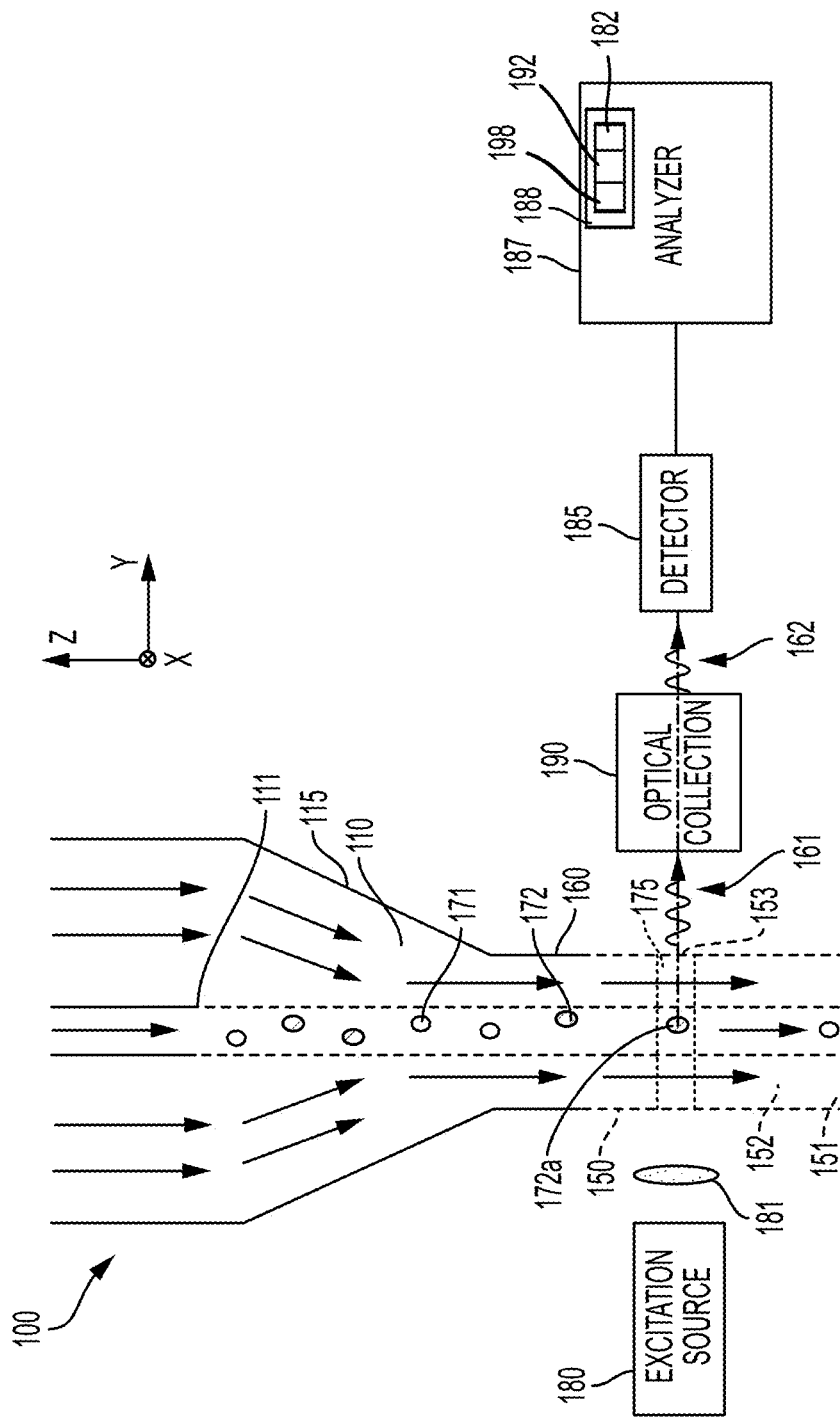
FIG. 1 is a diagram of a discrimination system in accordance with certain embodiments.

Embodiments described herein relate to devices, systems and methods for discriminating between different types of objects. The objects emanate output light in response to an excitation light that is directed toward the objects in a fluid column, such as a flow stream. As used herein the term "emanate" refers to both reflected and fluoresced electromagnetic radiation, such as light. As used herein the term "light" refers to both electromagnetic radiation at wavelengths in the visible spectrum as well as electromagnetic radiation at wavelengths in the infrared and ultraviolet spectrums. Such output electromagnetic radiation may include light reflected or fluoresced directly from an object as well as light reflected or fluoresced by a stain or dye associated the object. In some implementations, cell types are distinguished based on the intensity of the output electromagnetic radiation emanating from the objects. Intensity can be determined as a peak intensity or even as a total intensity, such as the integrated area under an intensity signal. Specific embodiments described herein are directed to distinguishing between X-chromosome sperm cells and Y-chromosome sperm cells. Further embodiments are concerned with distinguishing viable X-chromosome bearing sperm cells from objects other than viable X-chromosome bearing sperm cells, including Y-chromosome bearing sperm cells and non-viable cells of both sexes.

It will be appreciated that the approaches of this disclosure can be applied more generally to distinguishing between any objects of different types so long as the output electromagnetic radiation emanating from one object type generates a discernable difference in at least one characteristic when compared to the electromagnetic radiation emanating from another object type. In some examples provided, the fluid column is a flow stream that has a curved boundary or interface where refraction of electromagnetic radiation may occur. For example, the curved boundary of the fluid column may be generally circular in cross section. The fluid column can be bounded by solid walls, such as within a cuvette or within a microfluidic channel, or may be jetted into the air, such as in a jet-in-air flow cytometer. The objects may move along the fluid column through a central core shaped by a sheath fluid that at least partially surrounds the central core. In the case of sperm sorting applications, the central core may comprise a core stream of sample fluid containing sperm cells. The core stream may be conditioned into a generally ribbon shape or may have a generally elliptical cross section for the purpose of orienting aspherical sperm cells. Electromagnetic radiation emanating from the objects encounters at least one optical refraction boundary between the objects and other materials, such as at the interface between the fluid column and air.

Due at least in part to the different refractive properties of sheath fluid and air, the light collection efficiency external to the fluid column of light emanating from objects within the column depends upon the position of the objects for such systems. Light collection efficiency that varies with position is detrimental in applications where the light emanating from the objects must be precisely quantified and such precision is limited by random (not directly observable) position fluctuations of the objects. In the case of sex differentiating sperm specifically, such systems seek to differentiate very bright and closely related fluorescence intensities. Sperm cells and sperm nuclei are generally stained with Hoechst 33342 to make such differentiations. Hoechst 33342 is a bright, cell permeable dye that binds selectively with the A-T base pairs in the minor grove of double stranded nuclear DNA. The stoichiometric staining of sperm cells with Hoechst 33342 differentiates X-chromosome and Y-chromosome as having slightly different amounts of nuclear DNA. For example, many domestic animals have about a four percent difference. When sperm cells are properly stained and oriented, this small difference can be distinguished by the fluorescence intensity of the Hoechst 33342 associated with the nuclear DNA of the sperm cells when they are irradiated with an appropriate excitation source, such as a laser operating at or near a wavelength of 355 nm.

This four percent difference is difficult to detect for several reasons. First, sperm nuclear DNA resides within the sperm head, which is aspherical or has a paddle-like shape in most species. This asymmetry causes sperm to fluoresce differently out the flat side and more narrow side. Indeed, this fluctuation exceeds the four percent difference in DNA content, meaning sperm must be oriented in order to be differentiated based on nuclear chromosomal content. Orienting geometries tend to produce a core stream having a ribbon shape, or an elliptical cross section. This elliptical cross section provides sperm larger than normal latitude for placement in one axis.

The approaches disclosed herein enhance the precision of systems that may be limited by such fluctuations, such as jet-in-air flow cytometers. As described in more detail below, the positional variability of light intensity collected from objects in a fluid column can be addressed with an algorithm that corrects for the dependence of intensity on position.

The approaches outlined herein are particularly applicable to flow cytometry. However, the approaches can be applied to any system where light is collected on one side of an interface from objects emanating the light from the other side of the interface, wherein the interface causes a variation in the emanating light ray paths in a manner dependent on the object's position relative to the detector. Approaches herein correct for positional variation within the fluid column thus providing more accurate measurements for distinguishing types of objects.

The "jet-in-air" flow cytometer system 100 illustrated schematically in FIG. 1 is one type of discrimination system that can be used to discuss the concepts of the disclosure. The "jet-in-air" flow cytometer system 100 includes a fluid column forming structure that creates a flow stream comprising a fluid column 150 that jets out of the exit nozzle 160 of the chamber 110 at high velocity, e.g., about 20 m/s. The fluid column 150 expelled from the exit nozzle 160 can be roughly circular in cross-section and may have a diameter of about 10 μm to about 100 μm in some implementations. In some embodiments, the interior of the chamber 110 and/or the exit nozzle 160 are configured with an internal geometry that hydrodynamically orients sperm within the fluid column. As a non-limiting examples the nozzles like those described in U.S. Pat. Nos. 6,782,768 and 6,263,745 may be incorporated for the purpose of orienting sperm and generating the coaxial flow of a fluid column. The fluid column 150 is composed of a core stream 151 within a sheath stream 152 where the arrows in FIG. 1 indicate the direction of flow of the core and sheath streams 151, 152. The sheath stream 152 may have a generally circular cross section, while the core stream has generally elliptical cross section, with a major and a minor axis.

Within the chamber 110, a sample injection element 111 introduces the core stream 151 containing objects 171, 172 which may be of multiple types. The core stream 151 is bounded by a sheath stream 152 comprising sheath fluid and shaped by hydrodynamic forces in the chamber 110. The sheath stream 152 at least partially surrounds the core stream 151, and the sheath stream 152 and the core stream 151 do not substantially mix. The sloping or angled walls 115 of the chamber 110 impart forces that shape the core stream 151 and accelerate objects 171, 172 within the core stream 151. The movement of the sheath stream 152 constrains the objects 171, 172 in the core stream 151 to move toward the center of the fluid column 150 when the fluid column 150 is ejected from the chamber 110. The fluid column 150 delivers the objects 171, 172 to a measurement region 175 of the fluid column 150, e.g., in single file.

As the objects pass through the measurement region 175 of the fluid column 150, light from an excitation source 180 provides excitation light to the objects 171, 172. The excitation source 180 can provide light in a broad wavelength band or in a narrow wavelength band. For example, the excitation source 180 may be a laser. Any laser suitable for producing a response from the object or a dye associated with the object may be employed. Pulsed lasers and continuous wave lasers are each well suited to produce appropriate responses. In some configurations, electromagnetic radiation generated by the excitation source, such as excitation light, may be modified by an optical element 181. For example, the excitation light may be focused on the measurement region 175 by a one or more lenses 181. Lenses may be used to focus the excitation electromagnetic radiation into a suitable beam shape focused on the measurement region. Objects 172a in the measurement region 175 emanate light, e.g., scattered or fluorescent light, in response to the excitation source 180.

Objects of a first type 171 will emanate output electromagnetic radiation that differs in at least one characteristic as compared to output electromagnetic radiation that emanates from objects of the second type 172. For example, in some scenarios, objects of the first type 171 will emanate light having a higher intensity than the light that emanates from objects of the second type 172.

An optical collection arrangement 190 is positioned to collect the output electromagnetic radiation 161 emanating from the object 172a within the measurement region 175 that crosses the optical refraction boundary of the fluid column 150 at the fluid-air interface 153. In some embodiments, the optical arrangement 190 may be configured to modify the output electromagnetic radiation 161 to provide modified output electromagnetic radiation 162 that focuses output electromagnetic radiation emanating from the object 172a in the measurement region 175 onto a detector 185. In some embodiments, the optical collection arrangement 190 may include an element that reduces the positional dependence of the output electromagnetic radiation 161. The detector 185 receives the modified output electromagnetic radiation 162 and, in response, generates an electrical signal representative of characteristics of the modified output electromagnetic radiation. As but an example, the detector 185 may be a forward fluorescence detector. Of course, other detectors may be incorporated to detect characteristics of interest, such as scatter, decay, phase shifts or other characteristics of interest. As but non-limiting examples, the detector may be a photomultiplier tube (PMT), silicon photomultiplier (SiPM) a photodiode array, or a split detector. In some embodiments, the detector 185 may represent more than one detectors. In some embodiments, a second position detector may be utilized. In other embodiments a side detector may be employed to detect side scatter or side fluorescence. Still other embodiments may incorporate both a position detector and a side detector in addition to the detector 185.

In some scenarios, the amplitude of the electrical signal may be different for different object types. The electrical signal is used by an analyzer 187 to distinguish between different types of objects 171, 172. For example, the analyzer 187 may be configured to compare the amplitude of the electrical signal to a threshold to discriminate between objects of the first type 171 and objects of the second type 172. The analyzer 187 may include one or more analog circuits and/or digital processors for manipulating one or more signals from one or more detectors. As but one example, a side detector may be employed 90 degrees relative to the detector 185 to detect side scatter or side fluorescence. In the case of sperm sorting, side fluorescence allows the analyzer 187 to differentiate properly oriented sperm from unoriented sperm.

The analyzer 187 may include a processor 188 having executable instructions stored thereon. In addition to those instructions 198 known for the purpose of collecting, comparing and manipulating information from detector signals, the processor may include instructions 192 for normalizing the intensity value of the output electromagnetic radiation in the represented in the electrical signal from the detector based on the position of the object 172a in the fluid column 150 at the measurement region 175. The intensity value may be normalized in any number of ways. As but one example, hand drawn lines or curves may be input by a user into a graphical user interphase based on an initial sampling of data including fluorescence intensities and positional information.

Figure 2:
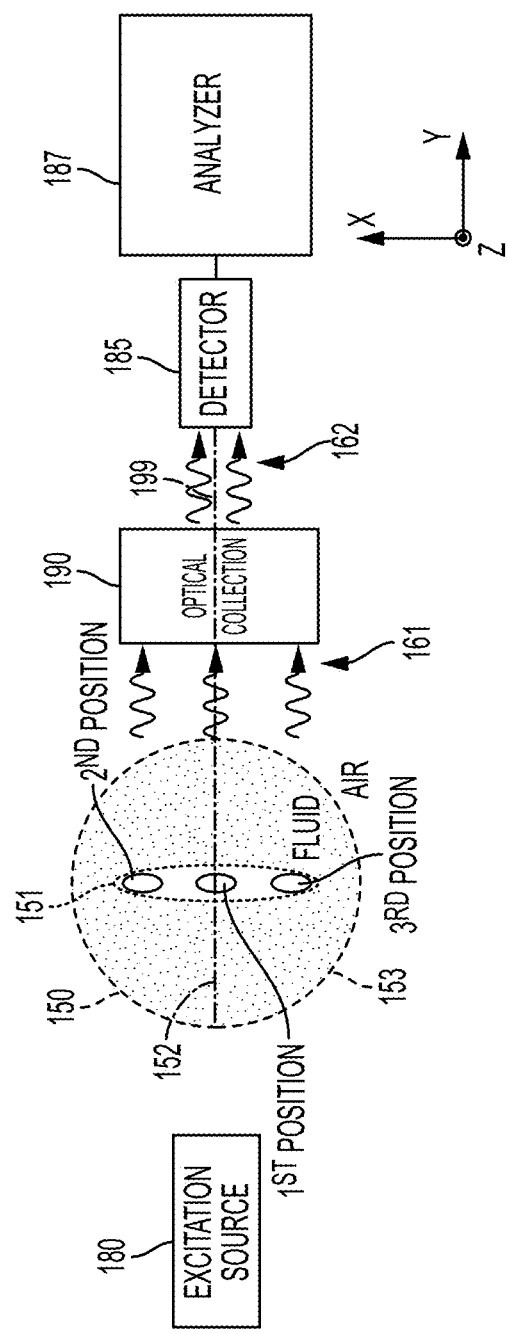
FIG. 2 shows an x-y plane cross section of the fluid column in the measurement region of the system of FIG. 1.

The processor 188 may also include instructions 182 for discriminating objects. FIG. 2 shows an x-y plane cross section of the fluid column 150 in the measurement region 175 depicted in FIG. 1. In the x-y cross section of the measurement region 175, the core stream 151 is elliptical in shape, and the fluid of the core stream 151 comprises at least one object 172a suspended in a buffer solution, which may also be referred to as sample. The sheath stream 152 substantially surrounds the core stream 151. In a particular example used for this discussion in this disclosure, the objects 171, 172 are sperm cells and the system 100 is implemented to discriminate X-chromosome sperm from Y-chromosome sperm.

A focused laser beam generated by the excitation source 180 irradiates the sperm cell 172a within the measurement region 175. The cells 171, 172 are stained with a fluorescent dye, and the excitation electromagnetic radiation causes the cell 172a within the measurement region 175 to emanate fluorescent output electromagnetic radiation. The purpose of the generally elliptical core stream 151 is to orient a sperm cell 172a such that the flat sides of the sperm cell are facing to the left and the right as shown in FIG. 2. In this orientation, the flat sides of the sperm cell 172a face the laser 180 and the optical collection arrangement 190, respectively. When each cell 171, 172 is presented in a similar orientation at the measurement region 175, random variability based on orientation can be greatly reduced. However, the elliptical cross section which aids in this orientation also provides significant latitude with respect to the position of the cell within the fluid column 150.

To obtain the desired orientation, the elliptical core stream 151, presents a major axis that parallels the x-axis depicted in FIG. 2. The sperm cell 172a can take any number of positions along the x-axis within the core stream 151. FIG. 2 shows three representative possible positions for the sperm cell 172a in the elliptical core 151, although it may be appreciated sperm may be located anywhere in between the depicted positions. In the orientation shown in FIG. 2, the first possible position for the sperm cell 172a in the core stream 151 is approximately at the center of the elliptical core 151 (on the optical axis 199 of the optical collection arrangement 190), a second possible position is at the top of the core stream 151 (above the optical axis 199), and a third possible position is at the bottom of the core stream 151 (below the optical axis 199). A position-dependent refraction of the output light rays emanating from the sperm cell 172a occurs at the fluid-air interface 153 at the different positions within the core stream 151. As used herein terms of relative position such as "top," "bottom," "upper," and "lower" should be understood as descriptive regarding the relationships between depicted features in the figures and not limiting on the claims, especially the position of sperm in a core stream 151.

When the sperm cell 172a is located at the first position and the fluid column 150 has a circular cross section as shown in FIG. 2, the in-plane rays of light emanating from the sperm cell 172a are approximately normally incident on the fluid-air interface 153. Rays that emanate from points of the sperm cell 172a away from its center, or rays that emanate out of the plane of the figure, are not exactly normally incident on the interface 153; these rays are not considered in this simplified discussion, but one of ordinary skill in the art can see how the discussion could be generalized to include them. Thus, to the extent any refraction of light occurs at the fluid-air interface 153 it occurs in a more uniform manner with respect to the detector 185.

Figure 3:
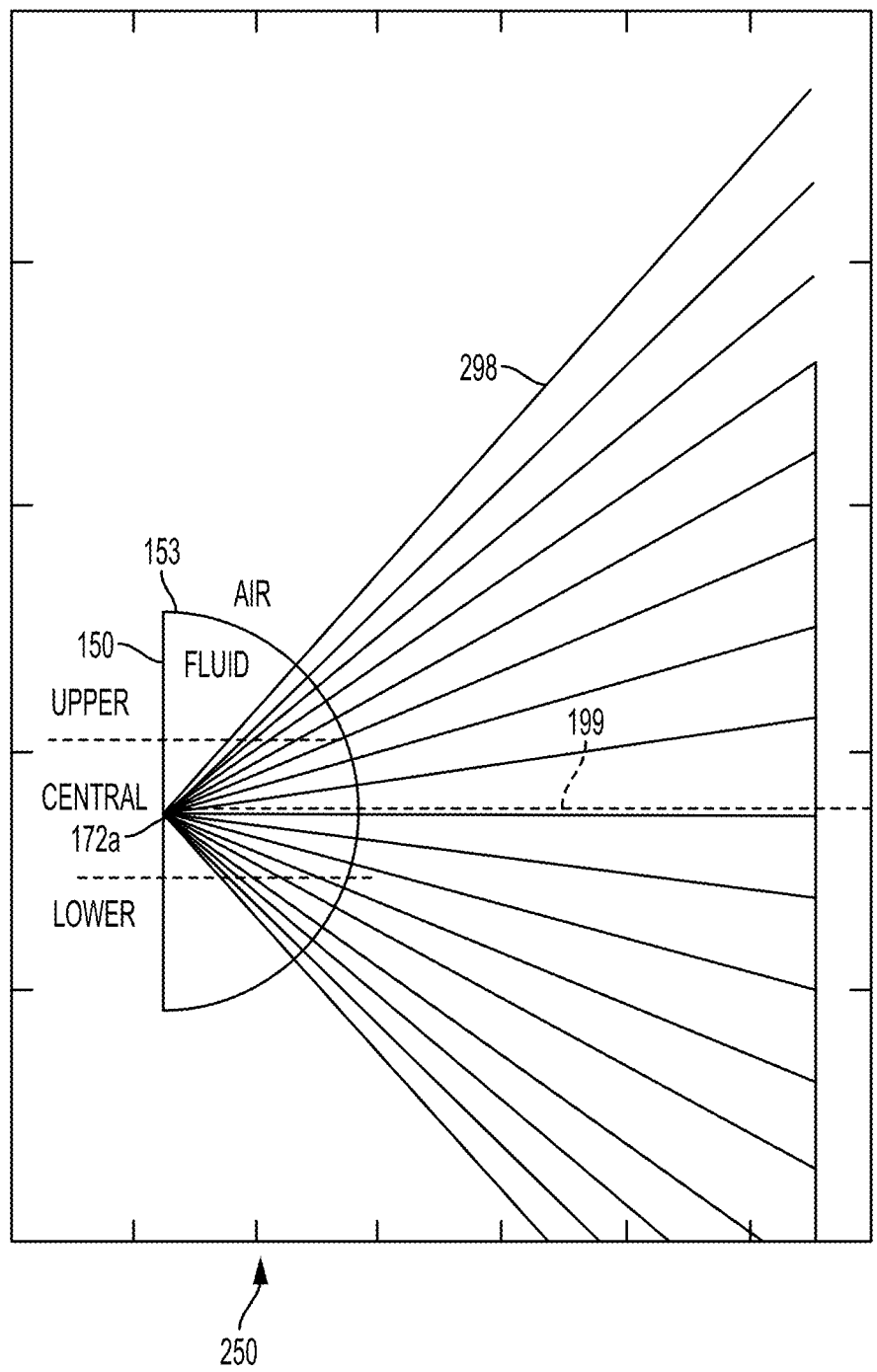
FIG. 3 shows light emanating from an object located near the center of the fluid column with substantially uniform refraction of light at the fluid-air interface of the fluid column relative to the optical apparatus functioning as the collection optics.

The diagram of FIG. 3 shows uniform light refraction of the output electromagnetic radiation 298 emanating from a sperm cell 172a as the electromagnetic radiation crosses the interface 153 when the sperm cell 172a is at the $1^{st}$ position within the elliptical core 151 shown in FIG. 2. Correspondingly, the in-plane density of the light rays 298 exiting the fluid column 150 in FIG. 3 is uniform with respect to ray angle. Uniform angular density of light rays corresponds to uniform radiance as a function of ray angle.

In contrast, when a sperm cell 172a is off the optical axis 199 and is nearer to the top or bottom of the elliptical core 151, e.g., at the $2^{nd}$ and $3^{rd}$ positions of the elliptical core 151 shown in FIG. 2, at least some of the output rays emanating from the sperm cell 172a encounter the fluid-air interface 153 at an oblique angle. These output rays are refracted in a non-uniform fashion at the fluid-air interface 153 in contrast to the normal incidence scenario described above. The most oblique rays are the most severely refracted. Refraction of the light rays causes the radiance distribution of the fluorescent light exiting the fluid column 150 across the fluid-air interface 153 to become non-uniform and to vary with position of the cell 172a along the x axis. That is, this refraction changes the radiance distribution of output electromagnetic radiation emanating from sperm cell 172a outside of the fluid column 150.

Figure 4:
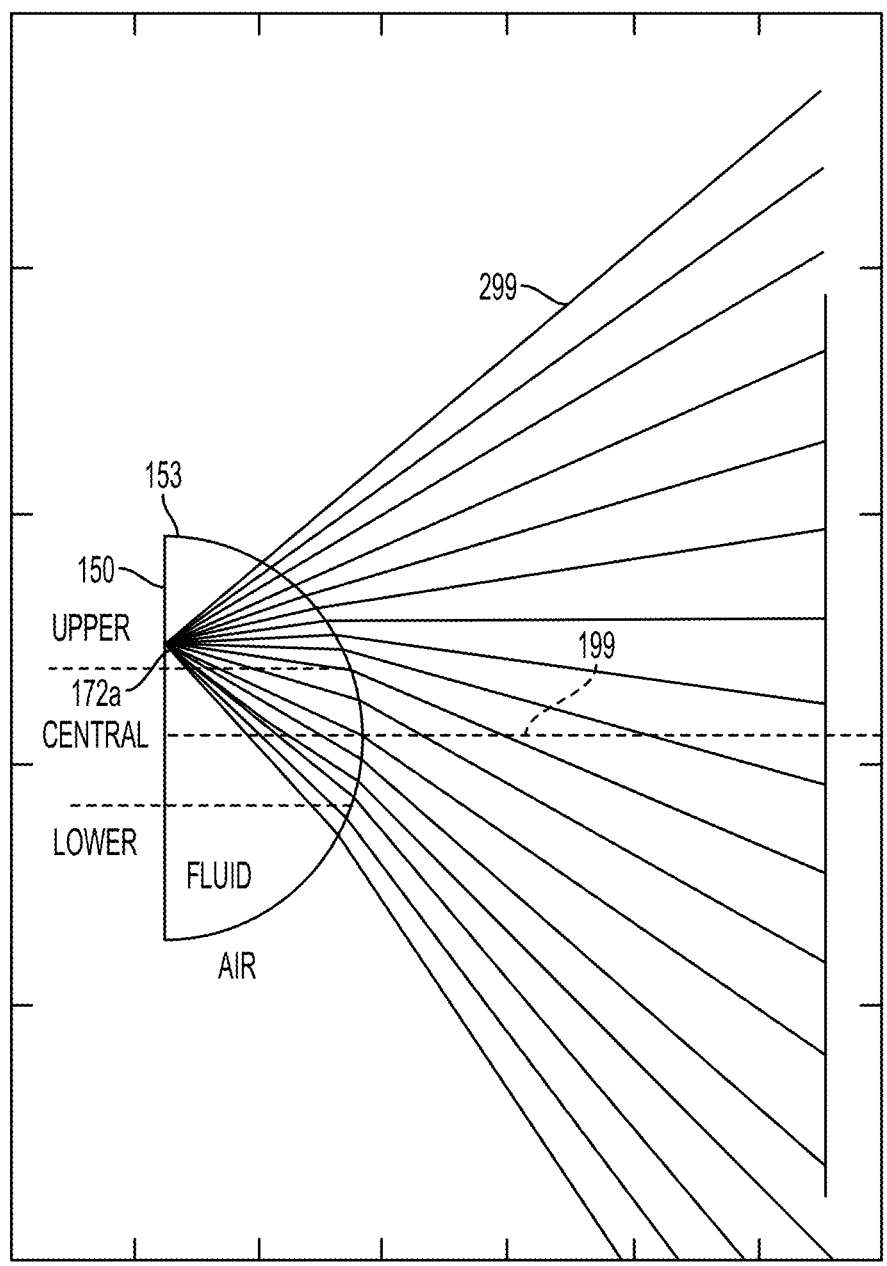
FIG. 4 shows light emanating from an object located in an upper portion of the elliptical core of the fluid column exhibiting non-uniform refraction of light at the fluid-air interface relative to the optical apparatus functioning as the collection optics.

For example, when the cell 172a is located off the optical axis 199, e.g., at the $2^{nd}$ or $3^{rd}$ positions shown in FIG. 2, the density of light rays and thus the radiance on the air side of the interface 153 is higher at positive or negative ray angles, respectively, with respect to the optical axis 199 when compared to the radiance on the air side of the interface 153 at angles parallel to the optical axis 199 or at negative or positive ray angles, respectively. Positive and negative refer to the sign of the ray angle γ in FIG. 5. FIG. 4 is a diagram illustrating light rays 299 emanating from a cell 172a and exiting the fluid column 150 through the fluid-air interface 153 when the cell 172a is located at the $2^{nd}$ position of the elliptical core 151. In this scenario, the density of light rays, or radiance, at positive ray angles is greater than the density of the light rays parallel to optical axis 199 or at negative ray angles. For an optical system with a predetermined numerical aperture (NA), the amount of light collected by the system from cells of the same type (e.g., the collection efficiency) may vary depending on whether the cell is in the first position or the second position. The positional dependence of the system collection efficiency leads to inaccuracies in determining cell type.

Figure 5:
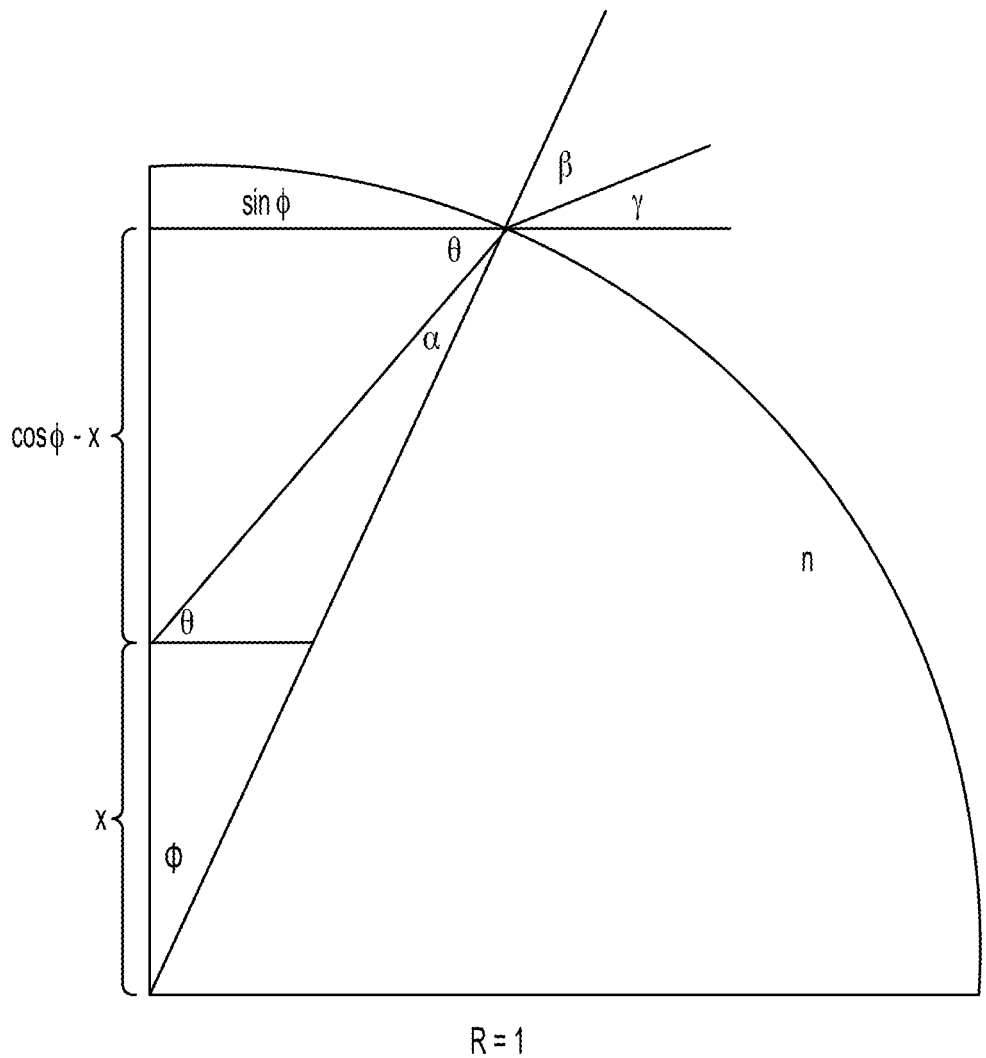
FIG. 5 illustrates the geometry utilized to develop an analytical formula for angular dependence of the in-plane light ray density as a function of position x.

With reference to FIG. 5, an analytical formula for the light ray density as a function of ray angle γ and sperm position x is determined using Snell's law, where γ is the angle of a light ray, with respect to the optical axis, emanating from the object after refraction at the fluid-air interface. This analysis considers only rays within, or tangential to, the two-dimensional cross-section of the flow stream.

We wish to solve for the density of the light rays with respect to the angle γ, which we can use to determine the density of rays at the entrance pupil of an optical collection system for each sperm position x. This can be written:

$$I_\gamma(\gamma). \qquad (1)$$

For our purposes we can assume that the sperm cell emanates light uniformly in all directions, so the density of emanated light rays with respect to the angle θ is:

$$I_\theta(\theta) = 1/\pi, \qquad (2)$$

that is, uniformly distributed from $$\theta = -\frac{\pi}{2} \text{ to } \theta = \frac{\pi}{2}.$$

By geometrical analysis:

$$\theta = \tan^{-1}\left(\frac{\cos\phi - x}{\sin\phi}\right); \qquad (3)$$

$$\alpha = \pi/2 - \phi - \theta; \text{ and} \qquad (4)$$

$$\gamma = \pi/2 - \phi - \beta, \qquad (5)$$

wherein the angles γ, θ, φ, α, β, and the distance x are shown in FIG. 5. As the flow stream has index of refraction n, Snell's law yields another relation between the angles:

$$\sin \beta = n \sin \alpha. \qquad (6)$$

The density of light rays external to the interface $I_\beta(\beta)$ is related to the density of light rays internal to the interface $I_\alpha(\alpha)$ by the following formula, with $T(\alpha)$ representing the average, across both polarizations, of the transmission through the interface:

$$I_\beta(\beta) = I_\alpha(\alpha)T(\alpha)\left|\frac{d\alpha}{d\beta}\right| \qquad (7)$$

The transmission is related to the Fresnel reflection coefficients for s- and p-polarization, $R_s(\alpha)$ and $R_p(\alpha)$, with the following formulas:

$$T(\alpha) = 1 - R(\alpha), \quad (8)$$

$$R(\alpha) = \frac{R_s(\alpha) + R_p(\alpha)}{2}, \quad (9)$$

$$R_s(\alpha) = \left|\frac{\cos\alpha - n\cos\beta}{\cos\alpha + n\cos\beta}\right|^2, \text{ and} \quad (10)$$

$$R_p(\alpha) = \left|\frac{\cos\beta - n\cos\alpha}{\cos\beta + n\cos\alpha}\right|^2. \quad (11)$$

Using Eq. (7) with the above and the following additional relations:

$$I_\phi(\phi) = I_\theta(\theta)\left|\frac{d\theta}{d\phi}\right|, \quad (12)$$

$$I_\alpha(\alpha) = I_\phi(\phi)\left|\frac{d\phi}{d\alpha}\right|, \text{ and} \quad (13)$$

$$I_\gamma(\gamma) = I_\beta(\beta)\left|\frac{d\beta}{d\gamma}\right|, \quad (14)$$

we have an expression for the density of rays with respect to γ:

$$I_\gamma(\gamma) = I_\theta(\theta)\left|\frac{d\theta}{d\gamma}\right|T(\gamma) \quad (15)$$

Now, the optical collection arrangement's NA is given by the sine of the maximum ray angle $\gamma_0$, so we can solve for this angle in terms of NA:

$$\gamma_0 = \sin^{-1}(NA) \quad (16)$$

Finally, the relative collected light intensity, as a function of sperm position x, is given by integrating Eq. (15) from $-\gamma_0$ to $\gamma_0$ and normalizing by that integral value at x=0:

$$\text{Relative Intensity} = \frac{\int_{-\gamma_0}^{\gamma_0} I_\gamma d\gamma}{\int_{-\gamma_0}^{\gamma_0} I_\gamma(x=0) d\gamma}. \quad (17)$$

Figure 6:
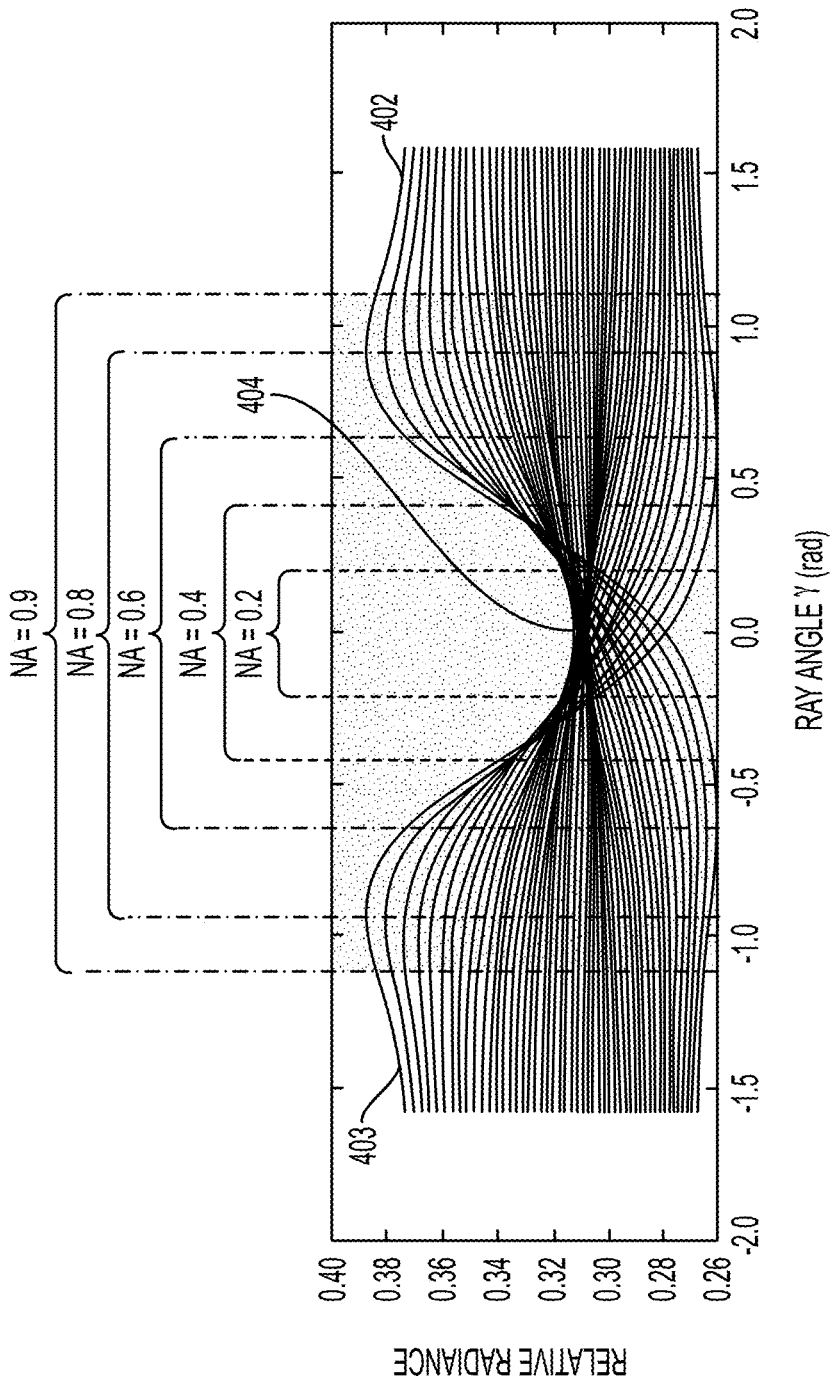
FIG. 6 provides a family of graphs showing the angular dependence of radiance for different object positions within a fluid column.

Using the formula for ray density distribution of Eq. (15), the angular dependence of ray density (radiance) for different sperm positions can be plotted as in FIG. 6. In FIG. 6, each of the lines represents the density of rays as a function of angle γ for a given sperm position x, where the angle γ is in radians. The plots correspond to a series of positions that lie in a range symmetric about x=0, (corresponding to graph 404 in FIG. 6), which is where the ray density (radiance) is uniform as a function of angle. When x is positive (e.g., $2^{nd}$ position in FIG. 2, corresponding to graph 402), relative radiance is higher for positive ray angles γ and lower for negative ray angles γ, and the opposite is true when x is negative (e.g., $3^{rd}$ position in FIG. 2, corresponding to graph 403).

Figure 7:
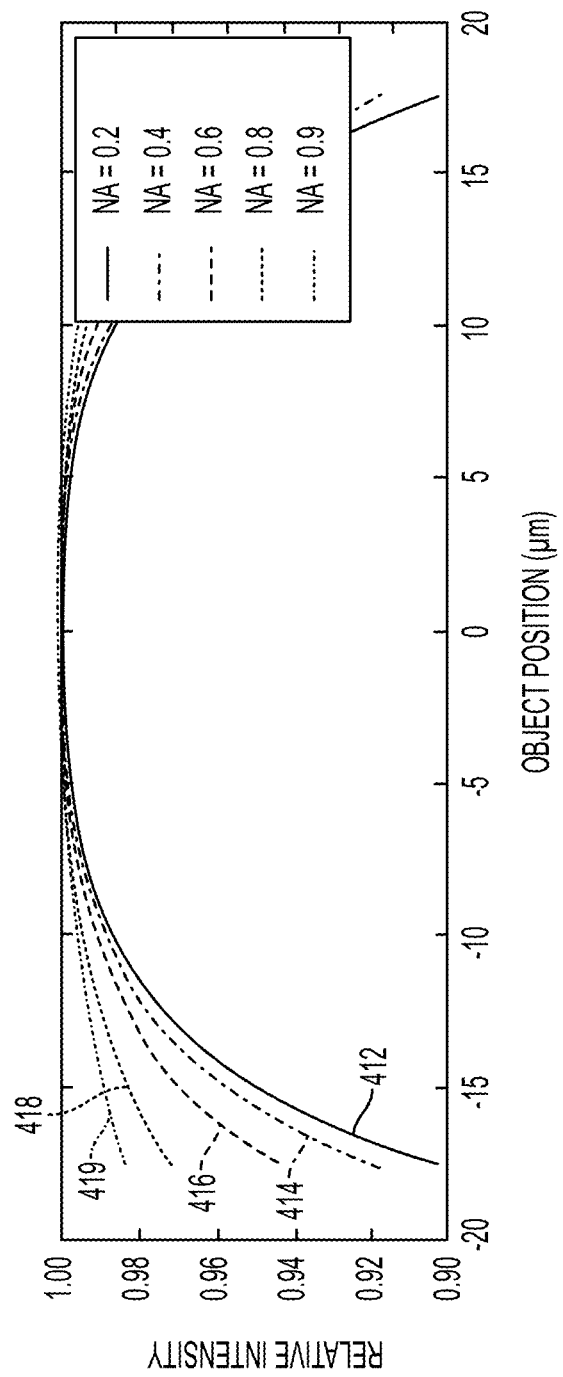
FIG. 7 provides a family of graphs of the relative intensity of light collected from the fluid column with respect to object position along the x axis for different numerical apertures of the collection optics.

If the numerical aperture of the collection optics (optical collection arrangement 190 in FIGS. 1 and 2) is large, e.g., approaching one, the variation in collected optical intensity with respect to position for light emanating from an object within the elliptical core is relatively small. This is because essentially all light emanating from the object and directed to the right would be collected by the collection optics, regardless of the exact ray direction, and the total amount of emanating light is invariant to object position (given uniform excitation). In contrast, a small numerical aperture results in a relatively large collected intensity variation with respect to object position, because changes in object position affect the radiance distribution, and a small numerical aperture implies only a portion of this changing radiance distribution is collected. Practical systems may have NAs that are significantly less than one, e.g., less than 0.5, or less than 0.3. The family of graphs provided in FIG. 7 illustrates the relative intensity of light collected from an object, as a function of object position x, through collection optics with different NAs. FIG. 6 illustrates the range of angles γ captured by the different numerical apertures of FIG. 7.

In the family of graphs of FIG. 7, graph 412 illustrates the relative intensity with respect to position along the x axis for collection optics (e.g., optical collection arrangement 190 shown in FIGS. 1 and 2) having a numerical aperture (NA) of 0.2; graph 414 shows the relative intensity with respect to position along the x axis for collection optics having an NA of 0.4; graph 416 shows the relative intensity with respect to position along the x axis for collection optics having an NA of 0.6; graph 418 shows the relative intensity with respect to position along the x axis for collection optics having an NA of 0.8; and graph 419 shows the relative intensity with respect to position along the x axis for collection optics having an NA of 0.9. It is clear from FIGS. 6 and 7 that collection optics having smaller NAs produce a larger variation in collected light intensity with respect to object position when compared to collection optics having larger NAs. Additionally, collection optics with larger NAs collect light rays having a wider range of refraction angles than collection optics having smaller NAs, and therefore have a higher overall collection efficiency.

With respect to sperm discrimination or sorting application in particular, it can be understood that the elliptical major axis of the core stream 151 (FIGS. 1 and 2) may be about 50 μm in length, providing sperm about 25 μm in latitude to move in either direction. Referring back to FIG. 7, it can be seen a NA of 0.2 only captures about 90% of an objects relative intensity when the object is about 17 μm off center. Similarly, a NA of 0.4 captures only 92% of the relative intensity for objects that are about 17 μm off center and a NA of 0.6 captures a little more than 94% of the relative intensity at the same position. It may be further appreciated that the NA of collection optics for a sperm sorter may be between about 0.3 and 0.6. While FIG. 7 illustrates the benefit of increasingly large numerical apertures, such numerical apertures are increasingly expensive and have a shallower field of depth, meaning the larger aperture must be placed closer to the nozzle. There is, however, a limit on how close the collection optics can be placed in sperm sorting applications. In typical sperm sorting instruments, the apertures may be between about 0.5 and 0.6. Embodiments described herein correct for the positional dependency on measured intensity allowing lower numerical aperture collection optics to perform like higher numerical aperture collection optics.

Sperm located in the core stream 151 at positions approaching the $2^{nd}$ and $3^{rd}$ positions of FIG. 2, therefore, emanate a significantly lower overall intensity of electromagnetic radiation that is ultimately detected for analysis and discrimination. Indeed, the core stream 151 may have an elliptical major axis that is about 50 μm in length at high event rates (in the magnitude of 60,000 events per second and greater). Some sperm will be off center by 20 μm or even up to about 25 μm either side of the $1^{st}$ position. In the context of extremely bright and closely related fluorescence signals, this variation can overshadow the roughly 4% difference in stained nuclear DNA differentiating X-chromosome bearing sperm from Y-chromosome bearing sperm.

Furthermore, increasing the number of events at a given sperm concentration within a sample of buffer requires increasing the volume of sample per unit time in the fluid column passing through the measurement region. Increasing the number of events detected per second in this manner also increases the elliptical cross section of the core stream within the fluid column, including the length of the major axis. As a natural consequence, and as those of skill in the art are aware, generally increasing the sorting speed by increasing the flow rate of sample decreases the sensitivity of sperm sorting equipment. Therefore, embodiments described herein not only improve sperm sorting precision at customary speeds, but may also provide for sperm sorting at increased overall speed in terms of throughput without suffering losses in fidelity.

Figure 8:
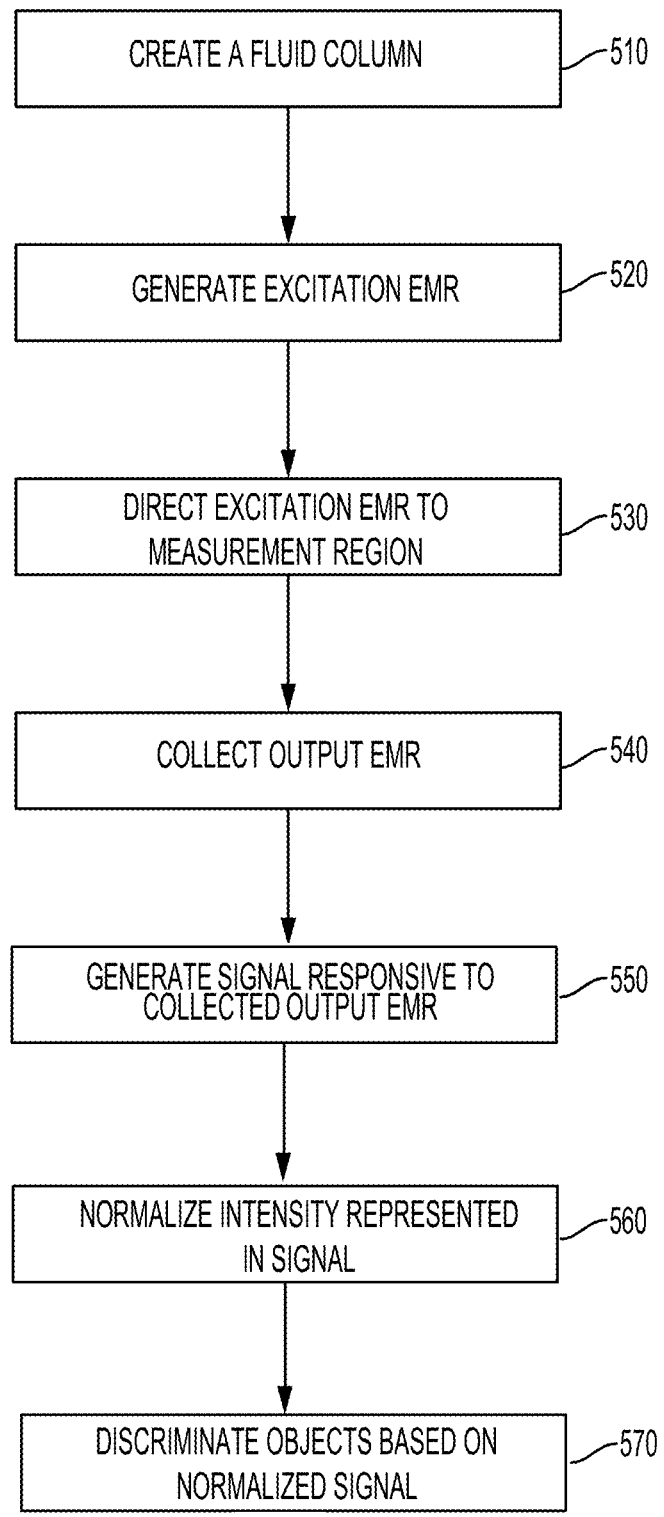
FIG. 8 is a flow diagram of an approach for identifying objects traveling in a fluid column by correcting for positional variation of detected output light in accordance with some embodiments.

An approach for identifying objects traveling in a fluid column in the presence of positional variation is illustrated in the flow diagram of FIG. 8. The process includes creating 510 a fluid column containing objects at differing positions within the fluid column. The fluid column may be a coaxial stream of fluid created by a jet-in-air flow cytometer. Such a fluid column may comprise a core stream with an elliptical cross section having a major axis along which objects may be positioned. The core stream may be coaxially contained within a sheath stream. In some embodiments the fluid column may have an air-fluid interface whereby refraction occurs. In other embodiments the fluid column may be formed within a cuvette or a microfluidic channel. In such cases there may be a liquid-glass interface and possibly a glass-air interface and emanating light may be refracted twice. Such twice refracted light is expected to benefit greatly from the angular dependency correction of certain embodiments.

The process continues by generating 520 excitation electromagnetic radiation and directing 530 the excitation electromagnetic radiation toward objects in the fluid column at a measurement region. Objects within the fluid column emanate output electromagnetic radiation in response to the excitation electromagnetic radiation at the measurement region. The output electromagnetic radiation is collected 540 from the objects in the fluid column, including objects having different position within the fluid column at a measurement region and a detector generates 550 an electrical signal responsive to the intensity of the output electromagnetic radiation collected by the optical arrangement.

Next, an analyzer or other suitable means normalizes 560 the intensity represented by the output signal based on the position of the object in the fluid column. The normalization may be performed by means of a correction, whereby signals generated off the central axis, such as toward and including the second and third positions of FIG. 2, are amplified by an appropriate correction factor based on their position. The magnitude of appropriate correction factors can be seen in FIG. 7. Once normalized by correction the method continues by discriminating 570 a first type of object from other objects. The discrimination may take place in a flow cytometer analyzer and may include one or more additional manipulations. For example, univariate histograms may be generated illustrating a distribution of fluorescence intensities. Bivariate histograms may also be generated with the corrected signal and with further calculated values. Such corrected and calculated values may be compared against gating regions in a flow cytometer analyzer or compared against look-up-tables to discriminate a first type of object from other types of objects.

As exemplary objects sperm may be discriminated as either X-chromosome bearing or Y-chromosome bearing sperm. Further, sperm may be stained with a DNA selective dye in addition to a secondary quenching dye. A quenching dye typically permeates membrane compromised sperm cells, such as dead or dying sperm cells, and greatly reduces the fluorescence produced by the DNA selective dye associated with those compromised cells. Such quenched cells are effectively removed from the closely related populations undergoing discrimination/sorting. In this way a system can discriminate live or viable sperm cells from dying or compromised sperm cells. The system may also discriminate viable X-chromosome bearing sperm from all remaining cells, Y-chromosome bearing sperm from all remaining cells, or even simultaneously viable X-chromosome bearing sperm and Y-chromosome bearing sperm from all other sperm cells.

FIG. 9 illustrates a first embodiment of the discrimination system substantially similar to the discrimination system depicted in FIGS. 1 and 2 in which output electromagnetic radiation 161 emanating from an object 172a located in the measurement region is collected by an optical collection arrangement 190. The optical collection arrangement 190 may include a collection lens that focuses a modified output electromagnetic radiation onto a detector 185. In the depicted embodiment, the detector functions to both measure a characteristic of the modified output electromagnetic radiation as well as a position detector 186 for determining the position of the object 172a within the core stream 151 of the fluid column 150.

The detector 185 suitable for determining both a characteristic of the modified output electromagnetic radiation 162 and for determining the location of the object 172a in the measurement region may comprise split detectors or a detector array of PMTs, SiPM, pin photodiodes or the like. These detectors may be located in the image plane of the object or in the Fourier plane to determine the position of the object. In the image plane the detectors directly measure the position of the object, whereas in the Fourier plane the position information will be extracted from the lateral intensity distribution (e.g. the left-right asymmetry).

Flow cytometry applications often require very sensitive (down to single photon counting) and fast (objects are moving with ~20 m/s through 10 μm) detectors. Detectors with the requisite speed and sensitivity are typically those detectors that provide an internal gain. In photomultiplier tube (PMT) or a silicon photomultiplier (SiPM), also known as pixelated avalanche photodiode, a single photon creates a cascade of up to about $10^6$ electrons. Both detector types are commercially available as detector arrays. SiPM may be better suited for use in detector arrays suitable for determining the position of the object because they are fabricated by standard techniques on silicon wafer. Some detector, such as SiPMs may be particularly well suited to be placed in a Fourier plane in order to distribute light over a larger area of the detector.

FIG. 10 illustrates an alternative embodiment in which a beam splitter 191, or other suitable optics, redirect a fraction of the power of the modified output electromagnetic radiation 162. The majority of the modified output electromagnetic radiation 162 is directed to and focused on the detector 185. In this embodiment the detector 185 comprises a first detector 176 for detecting a characteristic of interest. The first detector 176 may be any detector conventionally suited to quantify the particular characteristic of interest. In typical flow cytometer applications photodiodes, photomultiplier tubes (PMTs) and silicon photomultipliers may be particularly well suited to detect scattered or fluoresced electromagnetic intensity.

The beam splitter 191 may comprise a dielectric mirror 197, however those of skill in the art will appreciate other suitable optical components such as cube beam splitters, prism beam splitters and the like may be used for redirecting a portion of the modified output electromagnetic radiation 162 power. Regardless of the manner in which the output power is split, a first beam fraction 164 is directed along a first path to the detector and a second beam fraction 165 is directed along a different path to a second detector 173 in the form of a position detector 177. The position detector can be a camera, a position sensitive device ("PSD") such as an isotropic sensor or a charged coupled device (CCD), split detectors, a detector array of PMTs, SiPM, pin photodiodes or the like.

Figure 11:
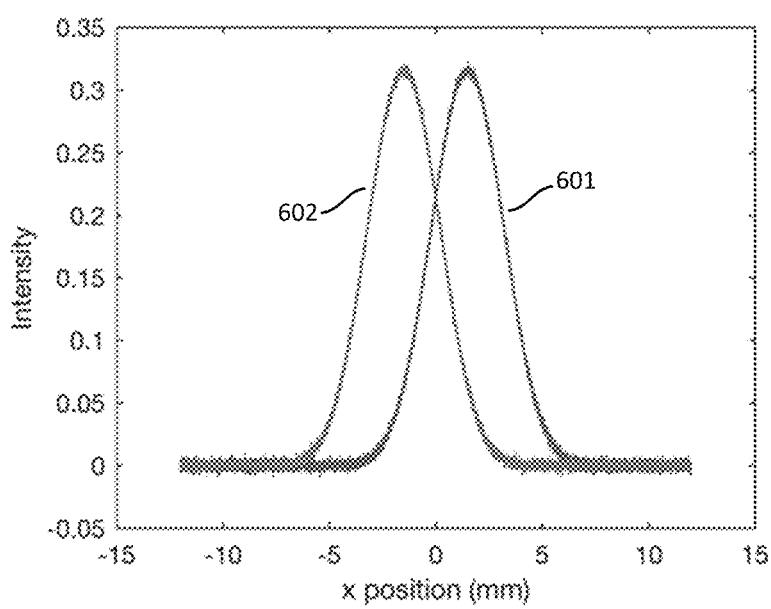
FIG. 11 illustrates the output of a simulation for determining object location with a split detector.

Turning to FIG. 11, a simulation was performed illustrating the viability of a split detector for determining positional information in a flow cytometry system. The simulation employed a split SiPM detector comprising 3 mm SiPM detectors mounted side by side. The edge at which the detectors met was calibrated as a central x coordinate position, simulating the beam axis of an interrogation laser as well as the symmetric center of a fluid column. A 1.5 mm spot size was swept across the split detectors from an x position between about −12 mm to 12 mm and the relative intensity was measured by each detector was recorded. A first graph 601 illustrates the relative intensity recorded for the beam spot from one of the detectors from x positions ranging from about −12 mm to about 12 mm, where the x position corresponds to a plane of the SiPM detector. A graph 602 illustrates the corresponding relative intensity detected by the other detector for the beam spot in a range of x positions from about −12 mm to about 12 mm. As can be seen, the positional difference in the two detectors results in differing measured intensities based on the x position of the 1.5 mm spot. These differences correlate to position and can be translated through processing means to approximate positional information. Noise was included in the simulation, but it was independent of intensity. At max intensity the noise corresponds to 0.8% coefficient of variation. The simulation demonstrated that x position can be determined in a split detector arrangement based on the relative intensity detected by each SiPM in a split detector arrangement. Those of skill in the art can appreciate, embodiments of the present invention are not limited to this configuration and that other detector configurations suitable for determining the position of a particle within a fluid column are also contemplated for use herein. As but one example, other detectors may be employed in a split detector arrangement. Those of skill in the art will appreciate that detectors should have low noise, as the combined signals must have a sufficiently low coefficient of variation.

Figure 12:
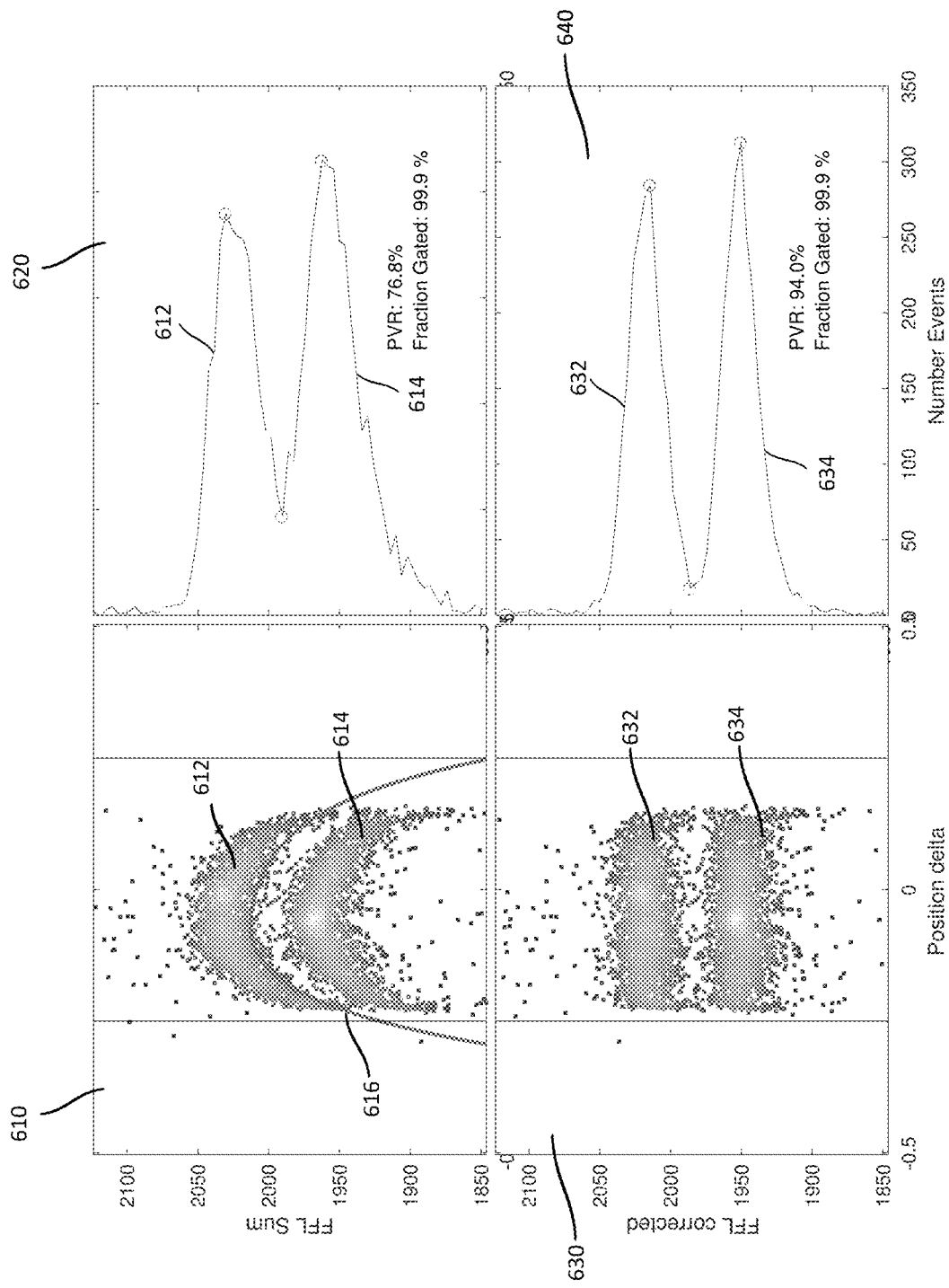
FIG. 12 illustrates the results of an experiment improving intensity measurements by correcting detected values based on the position of sperm nuclei.

FIG. 12 illustrates the result of an experiment incorporating positional correction for sperm nuclei in a fluid column resulting in significant improvements in differentiating X and Y-chromosome bearing sperm nuclei. Sperm nuclei stained with Hoechst 33342 were processed through a Genesis III sperm sorting instrument manufactured by Cytonome. The instrument was outfitted with a SiPM split detector. Sample and sheath pressure were adjusted to establish an event rate of 35,000 events per second. Nuclei were interrogated with a Coherent Genesis CW-355 laser at an average power of 150 mW. Plot 610 depicts a bivariate histogram illustrating a sum of fluorescence intensives from each detector in the split detector plotted against the positional delta of nuclei in the fluid column. As previously described, the range of the positional delta represents the major axis of the elliptical core stream along which nuclei may enter the measurement region. A population of X-chromosome bearing nuclei 612 is seen in a crescent shape. As expected, measured intensities are greatest near a position delta of 0 with reductions curving downward as nuclei move away from the central position. A population of Y-chromosome bearing nuclei 614 is seen as a second crescent just below the X population and, again, the highest intensities are seen near a position delta of 0 with significant losses in relative intensity as the nuclei move away from the central position.

Plot 620 presents a univariate histogram of the summed fluorescence intensities that corresponds to the intensities charted in plot 610. While the distinct population of X-chromosome bearing nuclei 612 and population of Y-chromosome bearing nuclei 614 can be seen, a comparison of plot 610 with plot 620 makes apparent that off center X-chromosome bearing sperm nuclei increasingly overlap with the well centered Y-chromosome bearing sperm nuclei. Indeed, the peak to valley ratio is calculated at 76.8%.

In accordance with embodiments of the invention, a correction factor 616 is illustrated as a curved line in plot 610. The correction factor 616 illustrates the degree of correction required to the detected fluorescence intensity to remove the variation introduced by the random positions of events. A corresponding correction was applied to the fluorescence sum values depicted in plot 630 to produce a corrected population of X-chromosome bearing nuclei 632 and a corrected population of Y-chromosome bearing nuclei 634. The corrected population of X-chromosome bearing nuclei 632 form a generally rectangular shape and no longer demonstrates fluctuation based on the position of the nuclei in the fluid column. A more distinct gap can be seen in plot 630 between the corrected population of X-chromosome bearing nuclei 632 and a corrected population of Y-chromosome bearing nuclei 634. Plot 640 illustrates the corresponding univariate histogram, which has a 94% peak to valley ratio between the corrected population of X-chromosome bearing nuclei 632 and the corrected population of Y-chromosome bearing nuclei 634. The stark contrast between plot 620 and plot 640 is visually apparent. Furthermore, the difference is a quantifiable with at 17.2 percentage points higher.

Figure 13:
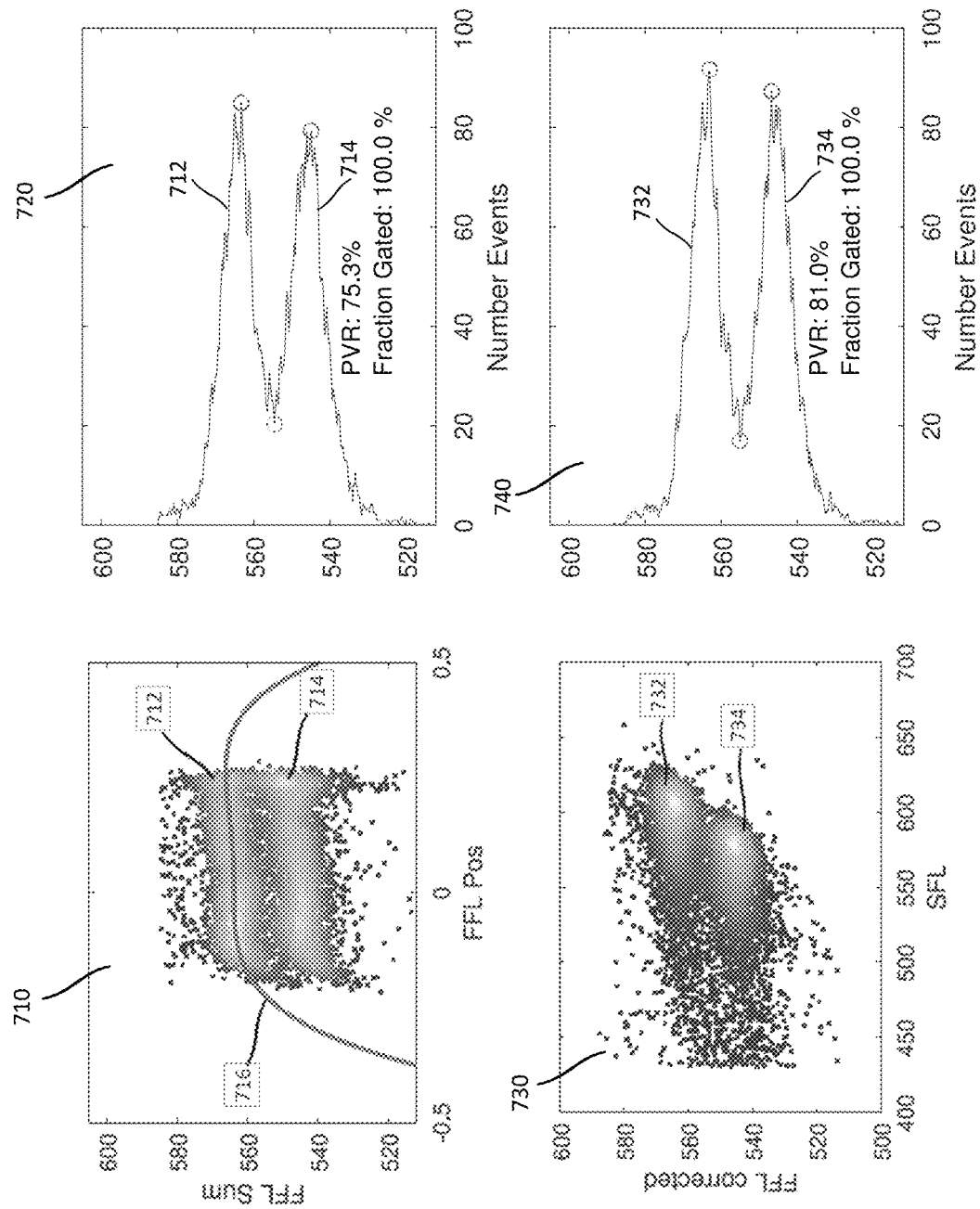
FIG. 13 illustrates the results of an experiment improving intensity measurements by correcting detected values based on the position of live sperm cells.

FIG. 13 illustrates the results of an example incorporating correction in accordance with embodiments described herein. Live sperm stained with Hoechst 33342 were processed through a Genesis III sperm sorting instrument manufactured by Cytonome. Sample and sheath pressures were adjusted to reach an event rate of 43,000 events per second and the sperm was interrogated with a Coherent Genesis CW-355 laser operated at an average power of 100 mW. Plot 710 illustrates a bivariate histogram of the summed fluorescence intensity and the relative positions of live sperm in the core stream. Again, the population of X-chromosome bearing sperm 712 can be seen as a first population above a population of Y-chromosome bearing sperm 714. A correction factor 716 for normalizing the summed intensity values is also depicted in plot 710. Plot 720 illustrates the univariate histogram of uncorrected summed intensities and demonstrates a peak to valley ratio of 75.3% between the population of X-chromosome bearing sperm 712 and the population of Y-chromosome bearing sperm 714.

Plot 730 provides a type of bivariate histogram common in sperm sorting applications. In this case, a corrected forward fluorescence intensity is plotted against a side fluorescence. A forward fluorescence vs side fluorescence histogram is useful for sorting live sperm because the side fluorescence provides information on the orientation of each cell. In contrast, sperm nuclei are sonicated and removed from the aspherical sperm head. As such, orientation is not an issue when sorting sperm nuclei. For this reason, nuclei are easier to sort and are often used to calibrate sperm sorting flow cytometers. Plot 730 depicts a corrected population of X-chromosome bearing sperm 732 and a corrected population of Y-chromosome bearing sperm 734

Much like the previous example, plot 740 still correlates in the Y axis to the corrected forward fluorescence of graph 730. In the univariate plot of graph 740, the corrected population of X-chromosome bearing sperm 732 and the corrected population of Y-chromosome bearing sperm 734 can be seen as more distinct peaks having a machine calculated peak to valley ratio of 81.0%. And again, the corrected histogram presents a significant improvement over plot 720 demonstrating the value of positional correction for live sperm.

In another aspect, embodiments described herein may provide systems and methods that substantially ease an alignment process in a flow cytometer. In the case of sperm for example, the measurement region, detectors, and even the structure forming the sheath flow must be properly and precisely aligned in order to generate and collect sufficiently clear signals for differentiating the very bright and closely related X and Y-chromosome bearing sperm populations. Even in a precise and proper alignment, oriented sperm in a fluid column can assume any number positions along the major axis of core stream. As described above with respect to FIGS. 3-7, this means that even when the components of the flow cytometer are in perfect alignment, there is an angular dependency to the detected output electromagnetic radiation. This angular dependency introduces noise like variations because the cells may be randomly positioned within the core stream.

In commercial sperm sorting applications, technicians typically undertake a number of course adjustments followed by a number of fine adjustments for multiple components in multiple axis in order to align the instrument. Due to the sensitivity of the instrument to each adjustment, the very closely related nature of the detected signals, and the number of possible adjustments, such alignments can be time consuming tasks for technicians operating sperm sorting instruments. When switching between samples machine alignments for commercially sorting sperm can take a few minutes, even up to five minutes. After declogging a nozzle or otherwise removing, replacing or adjusting other components that require calibration, it may take a technician 5 minutes, 15 minutes, and in rare cases as long as 30 minutes in order put an instrument in suitable alignment for commercially sex sorting sperm.

Figure 14:
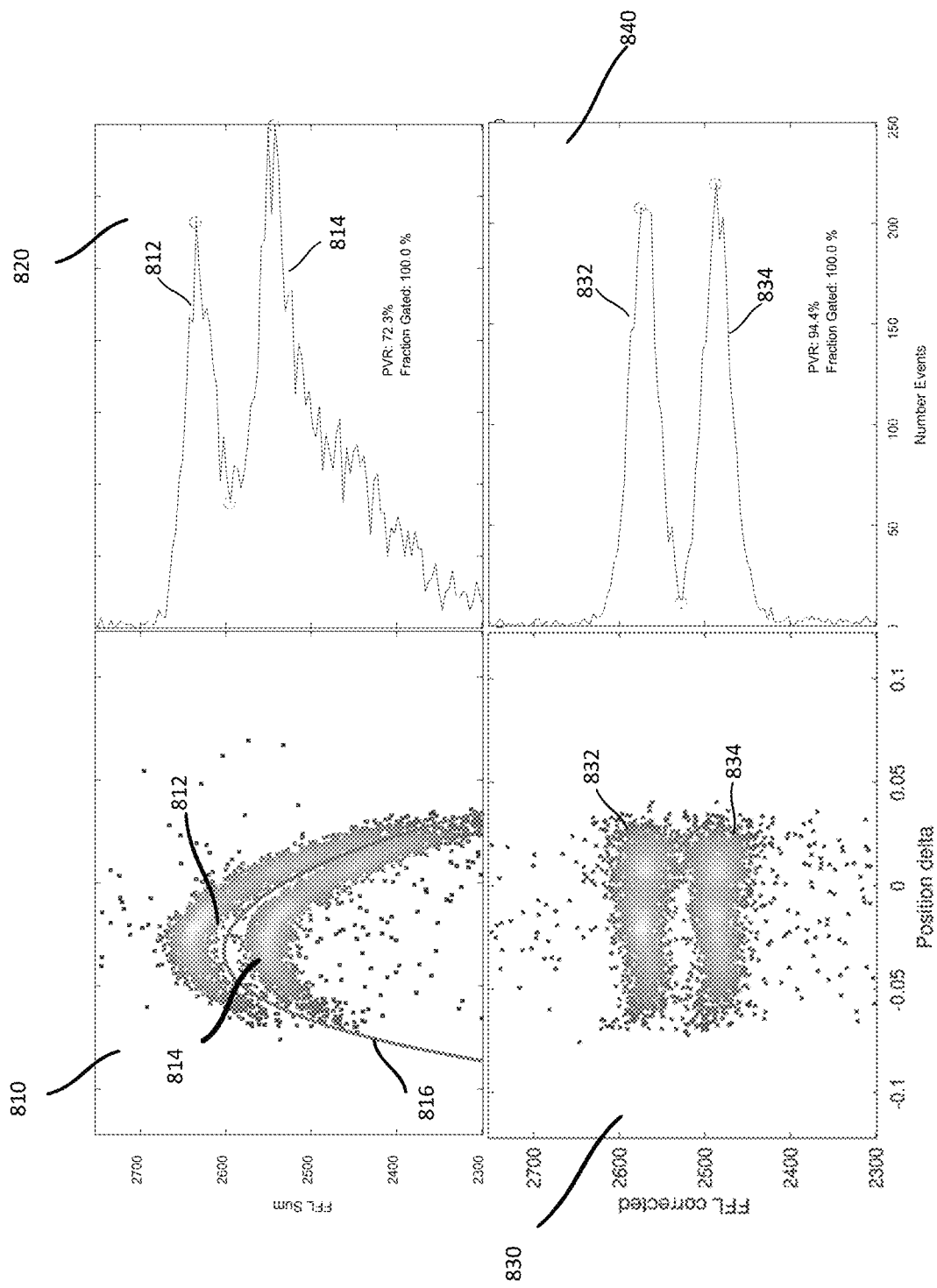
FIG. 14 illustrates the results of an experiment seeking to improve the performance of a poorly aligned instrument with a correction factor based on sperm nuclei position.

FIG. 14 illustrates the results of an example in which the alignment process is greatly reduced for discriminating sperm nuclei. Sperm nuclei stained with Hoechst 33342 were processed through a Genesis III sperm sorter manufactured by Cytonome. The instrument was fit with an SiPM split detector. The forward fluorescence detection was aligned for less than one minute resulting in a rough alignment. Sperm nuclei were run at an event rate of 33,000 nuclei per second and interrogated with a Coherent Genesis CW-355 laser operated at an average power of 150 mW. Plot 810 illustrates the bivariate histogram showing the summed forward fluorescence plotted against the position detected by each event by the SiPM. The poor alignment is evident in each of the population of X-chromosome bearing nuclei 812 and the population of Y-chromosome bearing nuclei 814. In poor alignment the crescent shapes are asymmetric and the fluorescence intensity values drop dramatically in the positive x direction as compared to the negative x direction. The population of Y-chromosome bearing nuclei 814 demonstrate the same skew.

The correction factor 816 is illustrated as a line between the two populations. This correction factor 816 illustrates the degree of correction that will be performed to summed fluorescence values at each x location. Stated differently, the correction factor 816, represents a curved line that will be normalized by correction to a flat line. Each summed fluorescence value at a corresponding x position along line receives the same magnitude of increase or decrease as the correction factor 816.

The distortion caused by rough alignment is more pronounced in the histogram of fluorescence intensities of plot 820, where increased overlap results in a peak to valley ratio of 72.3% between the population of X-chromosome bearing nuclei 812 and the population of Y-chromosome bearing nuclei 814.

In plot 830, the corrected forward fluorescence summed value is plotted in a bivariate histogram against the detected position of each event. It can be seen, again, that by normalizing the fluorescence intensity values with a correction factor 816 based on the position of the cells, two clean populations of cells emerge. A corrected population of X-chromosome bearing nuclei 832 and a corrected population of Y-chromosome bearing nuclei 834 are more clearly and distinctly grouped in plot 830. Importantly, the orthogonal relationship of these populations translates in the univariate fluorescence intensity histogram seen in plot 840, where two distinct univariate peaks have a calculated peak to value ratio of 94.4%.

In addition to the use of correction, some embodiments disclosed herein include elements that reduce the variation in collected light intensity with respect to object position in a flow stream. Some embodiments described herein can provide modified output light that has less than about a 3%, or less than about a 2%, or even less than about a 1% measured intensity variation for a deviation in position of the object that is less than 60% of a radius of the flow stream away from a center of the flow stream along an axis perpendicular to the optical axis. Many applications are sensitive to intensity measurement errors, which may arise from a variety of sources. Due to the difficulty in reducing intensity fluctuations by precisely controlling the position of objects within the flow stream, it is useful to instead reduce the variation in collected light intensity with respect to object position by careful design of the optical collection arrangement. For applications such as X/Y sperm sorting, it is often the case that two or more cell populations are to be separated based on the difference in measured fluorescence intensity between the populations. If the random position fluctuations lead to fluctuations in collected light intensity that are greater in magnitude than the nominal difference in fluorescence intensity of the two populations, it is not possible to distinguish them with simultaneously high yield and high purity. The fluorescence intensity difference between X and Y sperm cells is typically only a few percent (e.g., ~4% for bovine sperm). Current sperm sorter systems can in theory achieve high throughput by increasing the flow rate of the core stream, but this has the effect of increasing the width of the core stream. Consequently, there would be a large uncertainty of the sperm position within the core of the flow stream. This position uncertainty and the resultant fluctuations in collected fluorescence intensity limit the maximum throughput of current sperm sorter systems to levels which do not obscure the small fluorescence intensity difference between X and Y sperm.

One approach for intensity-position correction may be understood with reference to FIGS. 6 and 7. The brackets in FIG. 6 highlight regions of integration that correspond to fluorescence collection optics with a given NA. Graphs of the collected intensity variation with respect to object position for the NAs of FIG. 6 are provided in FIG. 7. In FIG. 7, for a given NA, integration over the fluorescence collection region is performed such that the intensity of collected light can be plotted as a function of each sperm position. It is evident from FIG. 7 that increasing the NA of the collection optics helps to decrease the influence of object position on the fluorescence intensity gathered via the collection optics.

In some embodiments collection optics (e.g., the optical collection arrangement 190 in FIGS. 1 and 2) may be modified with elements that reduce collected light intensity variation with respect to object position as described above. Such embodiments are described in more detail in U.S. patent application Ser. No. 16/133,531, which is incorporated herein by reference. According to some such embodiments, the collection optics operate by masking certain rays in "angle space", that is, the collection optics selectively collect, attenuate, and/or block rays from different angles γ in order to achieve a desired intensity vs. position profile. In practice, an "angle space" masking function can be applied at a pupil (e.g., entrance pupil, exit pupil, or aperture stop) of an optical system, where the position of a ray intersection with the pupil plane corresponds to the angle γ. In some embodiments, the collection optical arrangement achieves a desired, e.g., flatter, intensity vs. position profile by preferentially collecting higher angle (pointing away from the optical axis) light rays to the exclusion of certain lower angle light rays.

Figure 15:
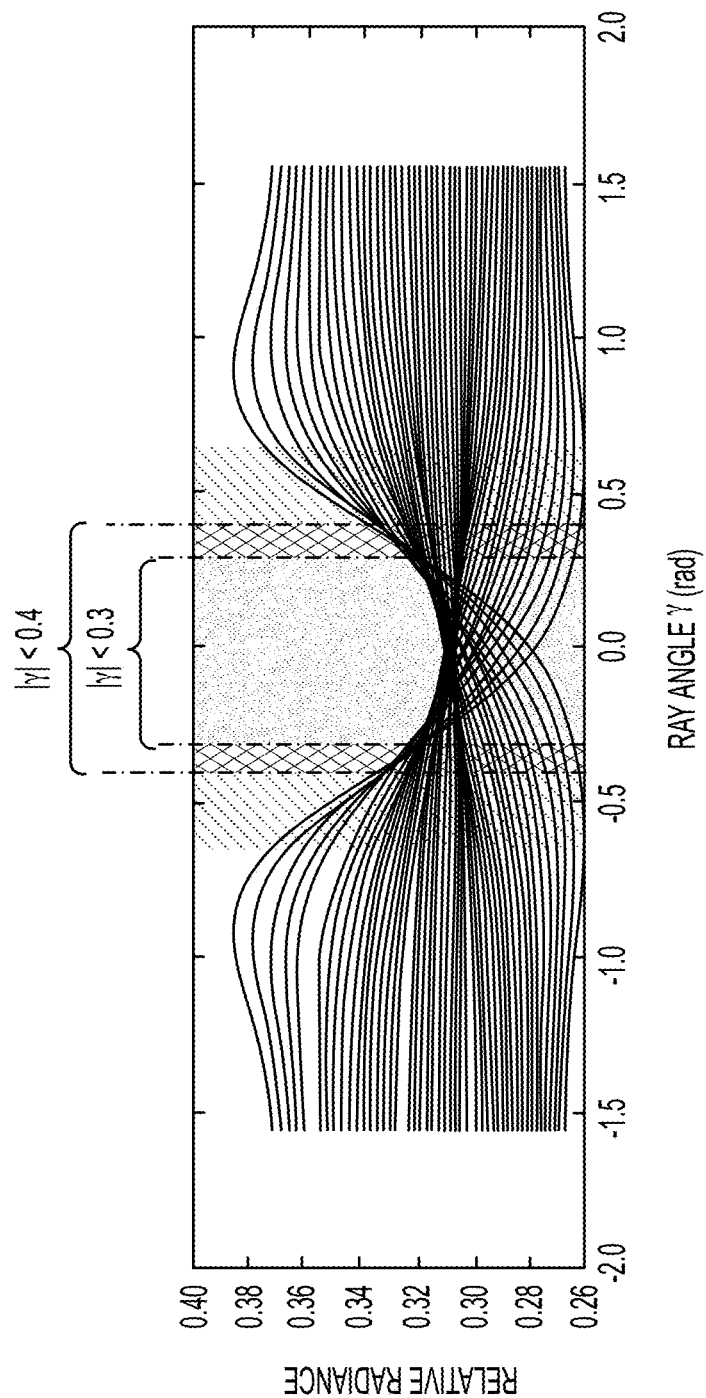
FIG. 15 provides a family of graphs of the angular dependence of radiance for different positions of the object and showing regions of exclusion.
Figure 16:
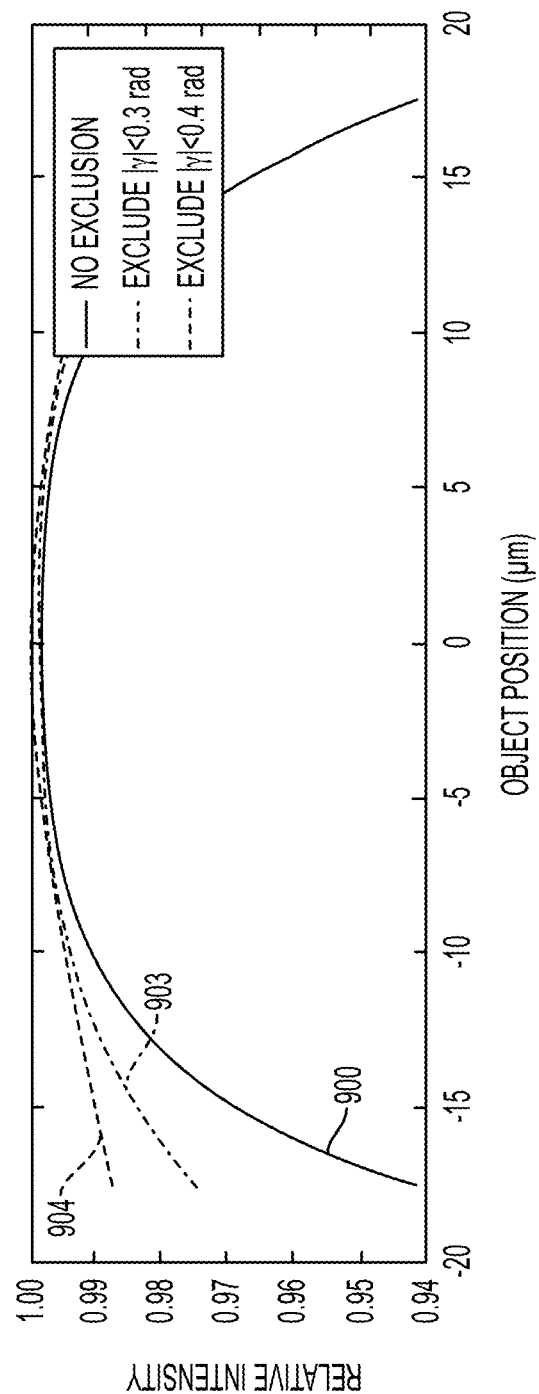
FIG. 16 shows the relative intensity of light collected from the fluid column with respect to object position along the x axis when no angles are excluded, when rays having angles between −0.3 rad and +0.3 rad are excluded, and when rays having angles between −0.4 rad and +0.4 rad are excluded.

FIGS. 15 and 16 illustrate how excluding low-angle refracted rays, at a given NA, causes the intensity-vs-position curve to flatten out. Excluding the low angle rays excludes the rays that produce the most variation in the intensity vs. position profile, whereas the angular variation of radiance at high positive angles tends to cancel the corresponding variation at high negative angles. FIG. 15 shows plots of the relative radiance vs. ray angle, γ, for different positions of the object along the x axis where the angle γ is in radians. In FIG. 15, each graph corresponds to an object position, x, within the core of a flow stream, as indicated in FIG. 5. The brackets in FIG. 15 show the portion of the light rays that will be excluded by the collection optics for each position x, when rays having angle magnitude less than 0.3 rad are excluded (bottom bracket in FIG. 15) and when rays having angle magnitude less than 0.4 rad are excluded (top bracket in FIG. 15).

FIG. 16 shows the relative collected light intensity vs. position of the object along the x axis when no angles are excluded (graph 900), when rays having angles between −0.3 rad and +0.3 rad are excluded (graph 903) and when rays having angles between −0.4 rad and +0.4 rad are excluded (graph 904). Graph 16 shows that when lower angle rays are excluded, the relative intensity vs. position graph exhibits less intensity variation with respect to position.

Figure 17:
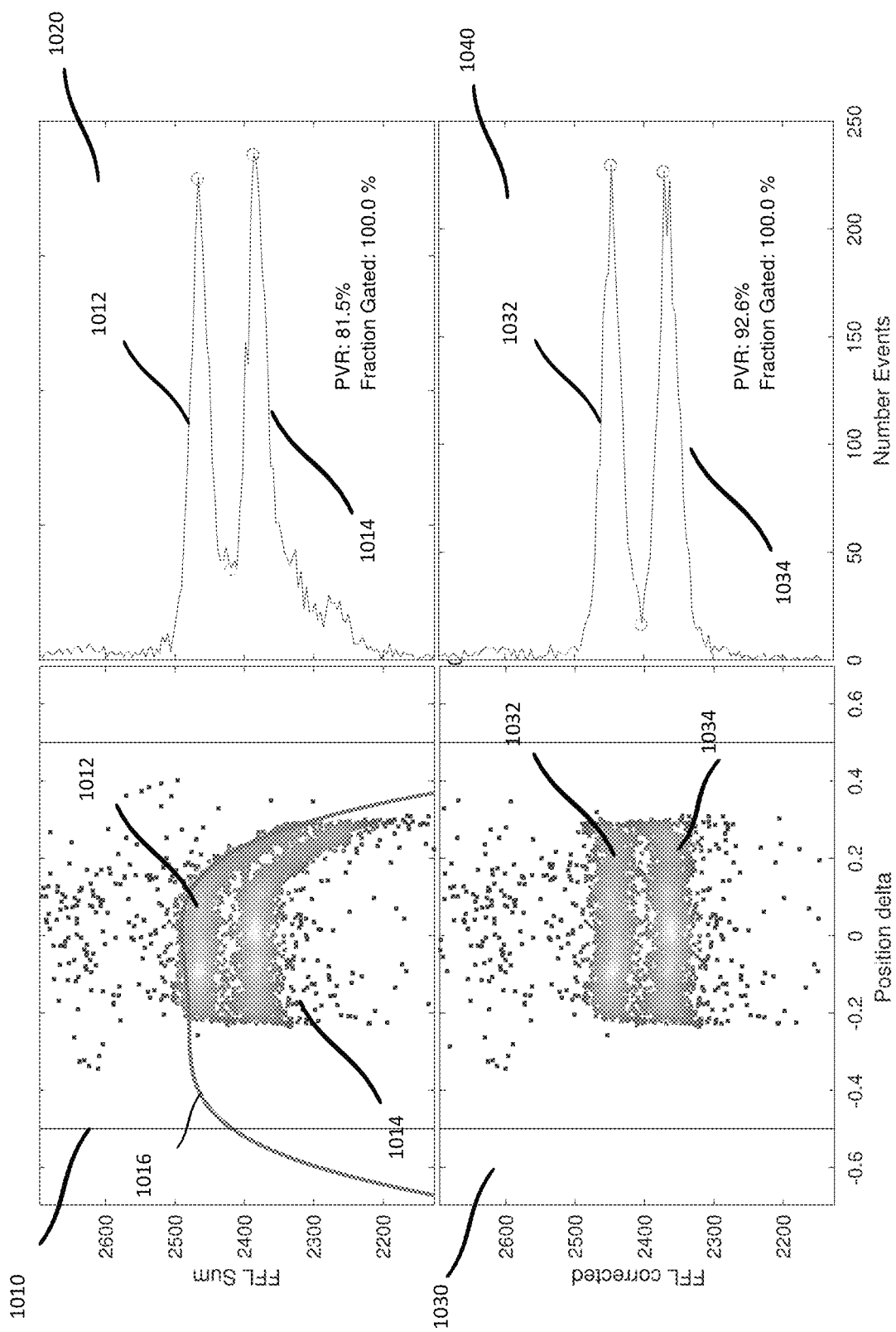
FIG. 17 illustrates the results of an experiment utilizing both a correction factor and an element for optically reducing the positional dependency of intensity measurements.

FIG. 17 illustrates the results of an experiment incorporating both a software based positional correction and a hardware based element in the collection light path that reduces collected light intensity variation with respect to object position as described. Sperm nuclei stained with Hoechst 33342 were processed through a Genesis III sperm sorter manufactured by Cytonome. The sperm sorter was fit with an SiPM split detector having a wire placed in the light collection path in order to exclude low collection angle electromagnetic radiation produced from the sperm nuclei. Suitable wires and other elements for blocking low collection angle electromagnetic radiation are described in U.S. patent application Ser. No. 16/133,531.

Sample and sheath pressures were adjusted to reach an event rate of 60,000 events per second and the nuclei was interrogated with a Coherent Genesis CW-355 laser operated at an average power of 90 mW. In plot 1010 it can be seen the wire mitigates some effect of the intensity dependence on nuclei position within the fluid column. There is still however, a significant decrease in relative intensity as nuclei move further in the positive direction along the x axis. A population of X-chromosome bearing nuclei 1012 and a population of Y-chromosome bearing nuclei 1014 are seen sagging significantly in the positive direction in the x axis. The corresponding peak to valley ratio calculated from the fluorescence intensity histogram of plot 1020 is 81.5%. Again, X-chromosome bearing nuclei that are located toward one end of the fluid column are not sufficiently detected. As a result, the summed fluorescence intensity of the nuclei at this end have similar intensity values as centered Y-chromosome bearing nuclei within the population of Y-chromosome bearing nuclei 1014. This skew is evident in the univariate histogram of plot 1020 in the form of a shoulder shifting downward and an exaggerated peak of the population of Y-chromosome bearing nuclei 1014.

A correction factor 1016 is illustrated on graph 1010. For each position, a correction value is added to the detected fluorescence intensity corresponding correction factor. Plot 1030 illustrates a bivariate histogram having a corrected population of X-chromosome bearing nuclei 1032 and a corrected population of Y-chromosome bearing nuclei 1034, which are more distinct rectangular populations. Plot 1040 provides the corresponding univariate histogram of corrected summed intensity values independent of the location of each event. The corrected population of X-chromosome bearing nuclei 1032 and the corrected population of Y-chromosome bearing nuclei 1034 are more distinct having roughly equal peaks heights and a peak to valley ratio of 92.6%.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

We claim:

1. A discrimination system, comprising:
   a fluid column containing cells at differing positions within the fluid column;
   an excitation source that generates excitation electromagnetic radiation directed toward cells in the fluid column at a measurement region, where the cells within the fluid column emanate output electromagnetic radiation in response to the excitation electromagnetic radiation;
   collection optics that collect output electromagnetic radiation from the cells;
   a detector that generates an electrical signal responsive to the intensity of the output electromagnetic radiation collected by the collection optics; and an analyzer having instructions stored thereon i) to normalize the intensity of the output electromagnetic radiation represented in the electrical signal based on the position of the cells in the measurement region, and ii) to discriminate a first type of cell from other cells.

2. The discriminating system of claim 1, wherein the detector comprises a first detector and wherein the system further comprises a second a detector that detects the position of cells in the measurement region.

3. The discriminating system of claim 2, wherein the second detector comprises a position detector.

4. The discriminating system of claim 3, wherein the position detector is one selected from the group of: a camera, a CCD, PSD, SiPM split detector, and photodiode array.

5. The discrimination system of claim 1, wherein the detector comprises a first detector that: i) generates an electrical signal responsive to the intensity of the output electromagnetic radiation collected by the collection optics and ii) detects the position of cells in the measurement region.

6. The discrimination system of claim 5, wherein the first detector is not located in an image plane of the collection optics.

7. The discrimination system of claim 5, wherein the first detector comprises one selected from the group consisting of a: PMT split detector, SiPM split detector, and photodiode array, an array of PMTs, and an array of SiPMs.

8. The discrimination system of claim 1, wherein the fluid column comprises cells in a generally elliptical cross section of core stream contained within a generally circular cross section of sheath fluid, and wherein cells in the measurement region are located at differing positions on a major axis of the generally elliptical cross section of core stream.

9. The discrimination system of claim 8, wherein the instructions stored on the analyzer for normalizing the intensity of the output electromagnetic radiation represented in the electrical signal based on the position of the cells in the measurement region applies a correction to the intensity of the output electromagnetic radiation represented in the electrical signal.

10. The discrimination system of claim 9, wherein the amount correction is determined for a cell at each position on the major axis of the core stream, and wherein the correction is applied to each event based on the position on the major axis of the core stream.

11. The discriminating system of claim 1, wherein the first type of cell comprises one selected from the group consisting of: viable X-chromosome bearing sperm; and viable Y-chromosome bearing sperm.

12. The discriminating system of claim 1, wherein the analyzer includes instructions for discriminating viable X-chromosome bearing sperm and viable Y-chromosome bearing sperm.

13. The discriminating system of claim 1, wherein the cell comprises sperm located within an elliptical column of sample fluid, where the sample fluid is formed coaxially with an outer layer of sheath fluid and the sheath fluid comprises a generally cylindrical shape.

14. The discriminating system of claim 1, further comprising an element that modifies the output electromagnetic radiation to increase the uniformity of output electromagnetic radiation collected by the collection optics of cells at different positions.

15. A detection system, comprising:
collection optics that collect output electromagnetic radiation from cells in a fluid column;
a detector that generates an electrical signal responsive to the intensity of the output electromagnetic radiation collected by the collection optics; and
an analyzer having instructions stored thereon i) to normalize the intensity of the output electromagnetic radiation represented in the electrical signal based on the position of the cells in the measurement region, and ii) to discriminate a first type of cell from other cells.

16. The detection system of claim 15, wherein the detector comprises a first detector and a second detector, where a mathematical operation on the electrical signal provided by the first detector is related to the position of cells in the fluid column based on a signal from the second detector.

17. The detection system of claim 16, wherein the second detector comprises a position detector.

18. The detection system of claim 17, wherein the position detector is one selected from the group consisting of: a camera, a CCD, PSD, SiPM split detector, and photodiode array.

19. The detection system of claim 15, wherein the detector comprises a first detector that: i) generates an electrical signal responsive to the intensity of the output electromagnetic radiation collected by the collection optics and ii) detects the position of cells in the fluid column.

20. The detection system of claim 19, wherein the first detector comprises one selected from the group consisting of a: PMT split detector, SiPM split detector, and photodiode array, an array of PMTs, and an array of SiPMs.

21. The detection system of claim 19, wherein the first detector is located outside the image plane of the collection optics.

22. The detection system of claim 15, wherein the fluid column comprises cells in a generally elliptical cross section of core stream contained within a generally circular cross section of sheath fluid, where cells in the fluid column are located at differing positions on a major axis of the generally elliptical cross section of core stream and wherein the instructions stored on the analyzer for normalizing the intensity of the output electromagnetic radiation represented in the electrical signal based on the position of the cells in the fluid column applies a correction to the intensity of the output electromagnetic radiation represented in the electrical signal.

23. The detection system of claim 22, wherein a correction factor is determined for each position on the major axis of the core stream, and wherein the correction factor is applied to each event based on the position on the major axis of the core stream.

24. The detection system of claim 15, wherein the first type of cells comprises one selected from the group consisting of: viable X-chromosome bearing sperm and viable Y-chromosome bearing sperm.

25. A method, comprising:
creating a fluid column containing cells at differing positions within the fluid column;
generating excitation electromagnetic radiation;
directing the excitation electromagnetic radiation toward cells in the fluid column at a measurement region, where the cells within the fluid column emanate output electromagnetic radiation in response to the excitation electromagnetic radiation;
collecting output electromagnetic radiation from the cells;
generating an electrical signal responsive to the intensity of the collected output electromagnetic radiation;

normalizing the intensity of the output electromagnetic radiation represented in the electrical signal based on the position of the cell in the fluid column measurement region, and discriminating a first type of cell from other cells.

26. The method of claim 25, further comprising detecting the position of cells in the measurement region.

27. The method of claim 25, wherein the fluid column comprises cells in a generally elliptical cross section of core stream contained within a generally circular cross section of sheath fluid, and wherein cells in the fluid column are located at differing positions on a major axis of the generally elliptical cross section of the core stream.

28. The method of claim 27 further comprising applying a correction to the intensity of the output electromagnetic radiation represented in the electrical signal.

29. The method of claim 28, further comprising determining a correction factor for each position on the major axis of the core stream and applying the correction factor to each event based on the position on the major axis of the core stream.

30. The method of claim 25, wherein the first type of cells comprises one selected from the group consisting of: viable X-chromosome bearing sperm; and viable Y-chromosome bearing sperm.

31. The method of claim 25, wherein the analyzer includes instructions for discriminating viable X-chromosome bearing sperm and viable Y-chromosome bearing sperm.

32. The method of claim 25, further comprising an element that modifies the output electromagnetic radiation to increase the uniformity of output electromagnetic radiation collected from cells at different positions.

\* \* \* \* \*